United States Patent [19]
Klug

[11] Patent Number: 5,854,009
[45] Date of Patent: Dec. 29, 1998

[54] METHOD OF DETECTING ESTROGEN-SENSITIVE PATHOLOGIES

[75] Inventor: Thomas L. Klug, West Chester, Pa.

[73] Assignee: Immuna Care Corporation, Bethlehem, Pa.

[21] Appl. No.: 715,406

[22] Filed: Sep. 18, 1996

Related U.S. Application Data

[60] Provisional application No. 60/003,966 Sep. 19, 1995.

[51] Int. Cl.$^6$ ..................................................... G01N 33/53
[52] U.S. Cl. .......................... 435/7.93; 435/7.1; 435/7.9; 435/7.92; 435/40.52; 436/543; 436/544; 436/545; 436/546
[58] Field of Search ..................................... 435/7.1, 7.92, 435/7.93, 40.52; 436/543, 544, 545, 546

[56] References Cited

FOREIGN PATENT DOCUMENTS 409176  1/1991  European Pat. Off. .

OTHER PUBLICATIONS

Magini et al. J. Steroid Biochem. 36:523–526, 1990.
Fishman et al. Cancer Res. 43:1884–90, 1983.
Harlow & Lane (1988) Antibodies, A Laboratory Manual. Cold Spr. Harbor Laboratory; Chapter 9, 10, & 14.
Arcos et al. (1965) Biochemistry 6:2032–9.
Bradlow et al. (1995) Ann. N.Y. Acad. Sci. 768:180,198.
Fishman et al. (1984) J. Steroid Biochem. 20:1077–81.
Fishman et al. (1980) Proc. Natl. Acad. Sci. USA 77:4957–60.
Galbraith et al. (1989) N. Engl. J. Med. 321:269–74.
Hellman et al. (1971) J. Clin. Endocrinol. Metab. 33:138–44.
Holzman, D. (1995) J. Natl. Can. Inst. 87:1207–9.
Ikegawa et al. (1983) J. Steroid Biochem. 18:329–32.
Ikegawa et al. (1982) Steroids 39:557–67.
Klug et al. (1994) Steroids 59:648–55.
Lindner et al. (1981) J. Steroid Biochem 15:131–6.
Michnovicz et al. (1990) Steroids 55:22–6.
Michnovicz et al. (1988) Steroids 52:69–83.
Newfield et al. (1993) Anticancer Res. 13:337–42.
Pazzagli et al. (1987) J. Steroid Biochem. 27:399–404.
Rader et al. (1973) Am. J. Obstet. Gynecol. 116:1069–73.
Samarajeewa et al. (1980) Steroids 36:611–8.
Schneider et al. (1982) Proc. Natl. Acad. Sci. USA 79:3047–51.
Sepkovic et al. (1995) Ann. N.Y. Acad. Sci. 768:312–6.
Zumhoff et al. (1968) J. Clin. Endocrinol 28:937–41.
Zumhoff et al. (1966) J. Clin. Endocrinol. Metab. 26:960–6.

*Primary Examiner*—Lila Feisee
*Assistant Examiner*—Geetha P. Bansal
*Attorney, Agent, or Firm*—Klauber & Jackson

[57] ABSTRACT

Diagnostic/prognostic methods are provided for screening for pathologies wherein an alteration in estrogen metabolism is indicative of a pathology or a susceptibility thereto which comprise detecting and/or quantifying directly in tissues and body fluids of mammals abnormal levels of estrone metabolites and their glucuronide conjugates. Particularly preferred methods involve the use of the 16OHE1-, 2OHE1- or 2MeoE1-glucuronide fraction, i.e., the fraction which contains the metabolite and its 3-glucuronide conjugate. Methods of preparing reagents to detect said 16OHE1-, 2OHE1-, and 2MeoE1-glucuronide fraction in tissues and body fluids are disclosed as well as test kits for performing the disclosed assays.

56 Claims, 12 Drawing Sheets

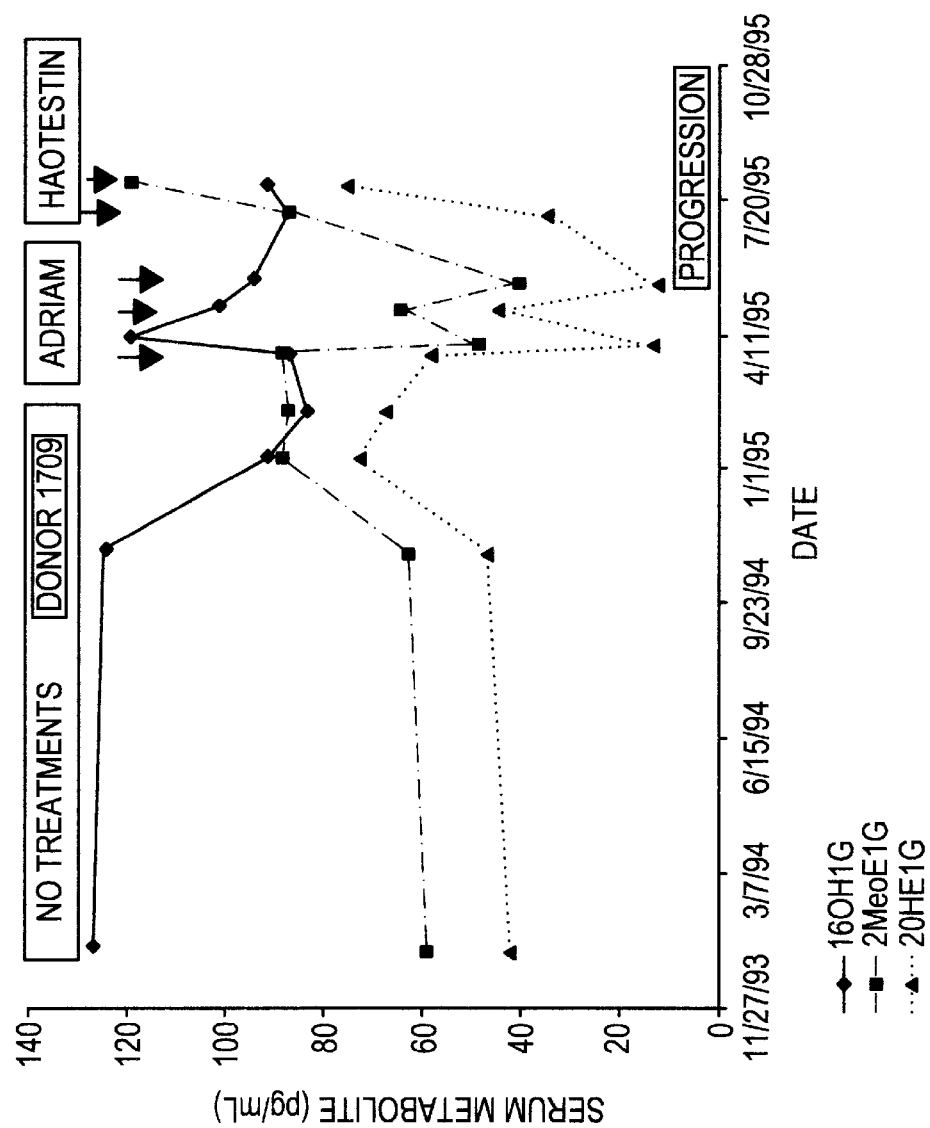

METHOD OF DETECTING ESTROGEN-SENSITIVE PATHOLOGIES

The present Application claims priority from U.S. Provisional Application Ser. No. 60/003,966, filed Sep. 19, 1995.

FIELD OF INVENTION

This invention relates to the medical arts, and more specifically, to the area of diagnostics/prognostics, particularly for oncology, utilizing immunochemical methods. The present invention thus relates to the use of estrogen metabolites, and especially, and 16α-hydroxyestrone (16OHE1) as well as conjugates thereof, and assays designed to detect and/or quantify in tissues and body fluids of mammals bearing a tumor burden, abnormal levels of estrogen metabolites and its conjugates. Particularly preferred metabolites for measurement are 2-hydroxyestrone, (2OE1) 2-methoxyestrone (2MeoE1), 16α-hydroxyestrone (16OHE1) and its glucuronides, and especially, the 2OHE1-, 2-methoxyestrone (2MeoE1), and 16OHE1-3-glucuronides.

BACKGROUND OF THE INVENTION

The mechanism for malignancy in mammalian cells has been and continues to be the subject of intense research. One of the most active areas is elucidation of the role of estrogens in the induction and maintenance of malignancies of estrogen-sensitive tissues such as cancers of the breast, endometrium, cervix, and ovary. The clear cut role of estrogens in the induction of breast cancer has led to a long search for evidence of estrogen excess in women with breast cancer.

Studies in this area have yielded contradictory results: patients with breast cancer have been reported to have elevated [Hellman L., Zumhoff B., Fishman J., et al.: J Clin Endocrinol Metab 33:138–144 (1971); Morreal C. E., Dao T. L., Nemoto T., et al.:J Natl Cancer Inst 63:1171–1174 (1979); Thissjen J. H., Poortman J., Schwartz E.: J Ster Biochem 6:729–734 (1975)], normal [Arguelles A. E., Poggi U. L., Saborida C., et al.: Lancet 1: 165–168 (1973); Bernstein L., Yuan J. M., Ross R. K., et al.:Cancer Causes and Control 1:51–58 (1990),]or decreased [Lemon H. M., Wotiz H. H., Parsons L., et al. :JAMA 196:1128–1136 (1966)] levels of urinary excretion of estrogens. Plasma and serum levels have been reported to be normal [Mancini A., DiPietro C., DeMarinis L., et al.:Gynecol Endocrinol 5:101–108 (1991); Sherman B. M., Wallace R. B., Jochimsen P. R.: Clin Endocrinol 10:287–296 (1979)], or elevated [Bernstein L., Ross R. K., Pike M. C., et al.:Br J Cancer 61:298–302 (1990); Drafta D., Schindler A. E., Milcu S. M., et al. J Ster Biochem 13:793–802 (1980)].

The use of antibodies against estrogens for immunohistochemical detection and/or quantitation of estrogens in fresh and fixed tumor tissues has also given controversial results. Kurman et al. in Cancer 42:1772–1783 (1978), initially demonstrated localization of estradiol in Sertoli-Leydig tumors of the ovary. Taylor and coworker in Cancer 47:2634–2640 (1981) extended the immunoperoxidase technique to paraffin-embedded tumor tissues taken from women with breast or endometrial cancer, finding that positive staining for estradiol correlated with cytosolic assays for the presence of estrogen receptor. Subsequent research in this area has been reviewed by Taylor [Taylor C., in Bennington, J. L. (ed), Major Problems in Pathology, Chapter 10, Vol 19; *Immunomicroscopy: a diagnostic tool for the surgical pathologist*. New York, Sanders, 1986, 233–237]. While the validity of this method for detecting estrogen receptors has been challenged by Chamness and McGuire in Arch Pathol Lab Med 106: 53–54 (1982), all investigators agree that an antibody measure of steroid in tissues may be related to endocrine responsiveness or prognosis of a tumor. Progress in the immunohistochemistry of steroids in tissues has been limited by the lack of antibodies of appropriately high affinity and, more importantly, by insufficient understanding of the structure of estrogen metabolites as they occur in tissues.

Previous research has used antibodies that recognize the unconjugated estrogens, not antibodies to conjugated forms of estrogen metabolites as in assays according to this invention. The importance of antibody specificity in immunohistochemical detection and/or quantitation of estrogens in fresh and fixed tumor tissues has not been appreciated prior to this invention. No previous researchers have demonstrated 2OHE1, 2MeoE1, 16OHE1 or its conjugates in normal or tumor tissues by any immunohistochemical method.

By contrast, there is evidence that malignancies may be associated with disturbances in estrogen metabolism rather than estrogen secretion, and increased 16α-hydroxylation of estradiol does seem to be present in both female animals and men and women with breast cancer. The metabolism of estradiol, the ovarian estrogen, is primarily oxidative (FIG. 1). There is an initial oxidation of estradiol to estrone (I, FIG. 1) which, in turn, is oxidized mainly by one of two alternative, irreversible pathways; 2-hydroxylation which leads to the relatively nonestrogenic metabolites 2-hydroxyestrone and 2-methoxyestrone (FIG. 1, VIII and VII, respectively), and 16α-hydroxylation which leads to the estrogenic metabolite 16α-hydroxyestrone (III, FIG. 1), among others. The relative contribution of the 16α-hydroxylation pathway is relatively constant under most biologic circumstances. There are at least two other oxidative pathways for estrogen; 4-hydroxylation which leads to 4-hydroxyestrone (4OHE1)(IX), and 15a-hydroxylation which leads to 15a-hydroxyestrone (15OHE1) (X). All of the aforemention metabolites, amongst others (FIG. 1) may be used by methods of the present invention. Alterations may also exist in conjugation of estrogens in tissues and body fluids. Research done on urinary estrogen metabolites indicates that urinary estrogens may be covalently conjugated as ethers or esters with glucuronic acids and/or sulphates, respectively, at the steroidal hydroxyl groups. Much less is known about the nature of estrogen metabolites in tissues and other bodily fluids. Hypothetical conjugates of 16OHE1 as they might occur in tissues and/or body fluids are illustrated in FIG. 2, conjugates of 2OHE1 in FIG. 3, and conjugates of 2MeoE1 in FIG. 4.

In 1966, Zumhoff and associates reported that men with breast cancer demonstrated markedly increased 16α-hydroxylation of estradiol [Zumhoff B., Fishman J., Cassouto J., et al.:J Clin Endocrinol Metab 26: 960-(1966)]. These same investigators subsequently reported increased formation and excretion of urinary 16α-hydroxylated estrogen metabolites in women with breast cancer after injection of radiolabelled estradiol [Hellman L., Zumhoff B., Fishman J., et al.:J Clin Endocrinol Metab 33:138–144 (1971)]. Fishman and colleagues later developed a new isotopic radiometric method that made it possible to measure the relative magnitudes of hydroxylation pathways more readily [Fishman J., Bradlow H. L., Schneider J, et al.:Proc Natl Acad Sci U.S.A. 77:4957–4960 (1980). This radiometric method involves injection into the animal under study of estradiol labelled with tritium at either the C-2 or C-16 position of the estradiol molecule. Oxidation in vivo at the C-2 and C-16 position frees the tritium from the labeled estrogen, and the radioactive tritium is released as tritiated water. Comparison of the relative amounts of tritiated water (counts per minute) in the serum and/or urine of the injected animal gives an estimate of the relative extent of 2- and 16α-hydroxylation in the animal.

Using this radiometric method, Fishman and coworkers greatly extended the study of 16α-hydroxylation and 2-hydroxylation in breast cancer by reporting the following findings: 1) increased 16α-hydroxylation, but unchanged 2-hydroxylation of estrogen was confirmed in women with breast cancer [Schneider J., Kinne D., Fracchia A., et al.:Proc Natl Acad Sci U.S.A. 79:3047–3051 (1982)]; 2) increased 16α-hydroxylation was found in women at familial high risk for breast cancer [Bradlow H. L., Hershcopf R. J., Martucci C., et al.:Ann NY Acad Sci 464:138≧151 (1986)]; and 3) Increased 16α-hydroxylation was found in mouse strains with high incidence of breast cancer, and the degree of increased risk paralleled the increase in 16α-hydroxylation [Bradlow H. L., Hershcopf R., Martucci C., et al.:Proc Natl Acad Sci U.S.A. 82:6295–6299 (1985). The afore cited radiometric studies found no significant alteration in 2-hydroxylation. This radiometric method is, however, not applicable to routine medical practice, and is complicated by the necessity to normalize the amount of tritium released to the injected animal's body volume. Moreover, no information as to the amounts or kinds of estrogens transformed by 16α-hydroxylation of estradiol is obtained by a radiometric method. Recognizing the limitation of the radiometric method, Fishman and co-investigators attempted to develop a radioimmunoassay (RIA) for unconjugated 16OHE1 using polyclonal antisera to 16OHE1 and tritiated 16OHE1 as tracer [Ikegawa S., Lahita R., and Fishman J.:J Steroid Biochem 18:329–332 (1983)]. RIAs done upon ethyl ether extracts of serum found very low levels of 16OHE1 in serum from normal men and women, averaging only 10 pg/mL in men and 5–16 pg/mL in women. Unfortunately, the researchers found that blank values for water, buffer, and steroid-free serum were also in the range of 5–18 pg/mL. The very low levels of 16OHE1 found in this assay, and its lack of reproducibility, obviously precluded its usage in further studies of the role of 16α-hydroxylation in breast cancer, and there are no reports of its use in any further studies. Yoshizawa and Fishman in J Clin Endocr 32:3–6 (1971), also attempted to develop an RIA for unconjugated 2OHE1 in methylene chloride extracts of serum. The later RIA found significant differences between clinical groups studied, but this assay was never used in studies of animals with cancer or other proliferative diseases. Emons and coworkers in Acta endocr, Copenh. 91: 158–166 (1979) developed an indirect radioimmunoassay for 2-methoxyestrone in human plasma, but did not apply that assay to studies of estrogen metabolism in disease. These same immunoassays were subsequently used by these investigators, however, in studies of estrogen metabolites in urine.

These assays also used the radioimmunoassay method and determined total urinary 2OHE1 and 16OHE1(normalized to urine creatinine concentration) after deconjugation of glucuronides and sulfates with enzyme treatment. For example, Michnovicz et al. in Steroids 52:69–83, 1988, found no significant difference in total urinary 16OHE1 secretion when comparing smokers and nonsmokers, but increased 2-hydroxylation in smokers; Galbraith and Michnovicz in N. Engl. J. Med 321:269–274, 1989, found no effect of cimetidine on urinary total 16OHE1 secretion, but reported a decrease in 2-hydroxylation; and, Michnovicz and Galbraith R., in Steroids 55:22–26, 1990, found no effect of thyroxine treatment on total 16OHE1 secreted in urine, but increased 2-hydroxylation with thyroxine treatment.

Finding no differences in urinary secretion of an individual urinary metabolite reflective of suspected alterations in estrogen metabolism associated with a specific pathologic condition, Fishman and coworkers developed a method for detecting alterations in estrogen metabolism which comprised isolating at least two metabolites of estrone from a biological sample and determining their quotient. This quotient, and/or changes in this quotient, are reported to be reflective of alterations in estrogen metabolism. This method forms the basis of European Patent Application No. 0113694.5, filed Jan. 17, 1990 by inventors Michnovicz et al. In regard to the utility of measurements of 16OHE1, the inventors state in this Application (page 2, line 24–25) that, ". . . the constitutive nature of this metabolite has discouraged its further consideration for either diagnostic or therapeutic purposes." Moreover, the method of Michnovicz et al. does not recognize the importance of measuring the glucuronide fractions of the estrogen metabolites, that is, the conjugated forms of metabolites.

As indicated above, several methods have been used to detect altered estrogen metabolism, especially increased 16α-hydroxylation in animals bearing tumors. These methods, however, are not applicable to human research and routine medical practice. Previous attempts to quantify 16OHE1 directly by RIA have failed to find measurable levels in serum. Therefore, there exists a need in the medical art for rapid, accurate, diagnostic tests for metabolites of estrone such as 2OHE1, 2MeoE1, and 16OHE1, assays that reflect altered metabolism and conjugation of estrogens in tissues and bodily fluids from animals. The invention disclosed herein meets said need by providing for non-invasive diagnostic/prognostic assays to detect and/or quantify in mammalian tissues and body fluids, preferably serum, estrogen metabolites such as 2OHE1, 2MeoE1, and 16OHE1 and their conjugates, preferably the sum of the free metabolite and its 3-glucuronide conjugate.

SUMMARY OF THE INVENTION

The present invention involves a method of screening for a pathology in mammals wherein an alteration in estrogen metabolism is indicative of the pathology or a susceptibility thereto which comprises detecting the level of a particular estrone metabolite and/or its glucuronide fraction from a biological sample taken from the mammal under examination; and comparing this level with an extrinsic numerical value derived either previously from the mammal under testing, or from the testing of other subjects of the same species, to detect any differences in the level of the particular estrone metabolite and its 3-glucuronide. A highly preferred embodiment involves the testing of serum or tissue to measure the level of the 2OHE1, 2MeoE1, and 16OHE1 glucuronide fraction to detect and/or monitor the growth of tumors in breast cancer.

The very different conclusions drawn from the prior art and that of the instant invention are due to the following distinctions between the prior art and the instant invention: 1) 2OHE1, 2MeoE1, and 16OHE1 metabolites are not totally deconjugated prior to assay in the present invention; 2) a specific conjugate of 16OHE1, substantially, the 2OHE1-, 2MeoE1-, and 16OHE1-3-glucuronides, are measured according to this invention, not total 2OHE1, 2MeoE1, or 16OHE1; and 3) the level of the 2OHE1-, 2MeoE1-, or 16OHE1-3-glucuronide in tissues and/or body fluids is useful by itself, without comparison or indexing to another estrogen metabolites or other substances.

OBJECTS OF THE INVENTION

It is thus an object of the present invention to provide diagnostic/prognostic methods useful for screening for pathologies wherein an alteration in estrogen metabolism is indicative of a pathology or a susceptibility thereto.

It is a further object of the present invention to provide a method for such screening which measures the level of the 16OHE1-glucuronide fraction, i.e., the fraction which contains 16u-hydroxyestrone (16OHE1) and/or its conjugate, 16OHE1-3-glucuronide.

It is a further object of the present invention to provide a method for such screening which measures the level of the 2OHE1-glucuronide fraction, i.e., the fraction which contains 2-hydroxyestrone (2OHFE1) and/or its conjugate, 2OHE1-3-glucuronide.

It is a further object of the present invention to provide a method for such screening which measures the level of the 2-MeoE1-glucuronide fraction, i.e., the fraction which contains 2-methoxyestrone (2-MeoE1) and its conjugate, 2-MeoE1-3-glucuronide.

It is a still further object of the present invention to measure the 16OHE1 glucuronide fraction, the 2OHE1-glucuronide fraction, or the 2-MeoE1-glucuronide fraction to detect and monitor the growth of tumors, especially tumors in breast cancer.

It is yet another object of the present invention to provide for specific diagnostic/prognostic assays to detect and/or quantify the 16OHE1-glucuronide fraction, the 2OHE1-glucuronide fraction, or the 2-MeoE1-glucuronide fraction in tissues, tissue extracts, and bodily fluids of mammals, and thereby detect tumors, assess their growth, stability, or regression, and provide valuable information for the diagnosis and prognosis of the malignant disease.

A still further object of the present invention involves the preparation of test kits which contain the necessary reagents and protocol for the performance of assays which can be used for the aforementioned screening assays.

BRIEF DESCRIPTION OF THE DRAWING FIGURES

The file of this patent contains at least one drawing executed in color. Copies of this patent with color drawings will be provided by the Patent and Trademark Office upon request and payment of the necessary fee.

Figure 7A:
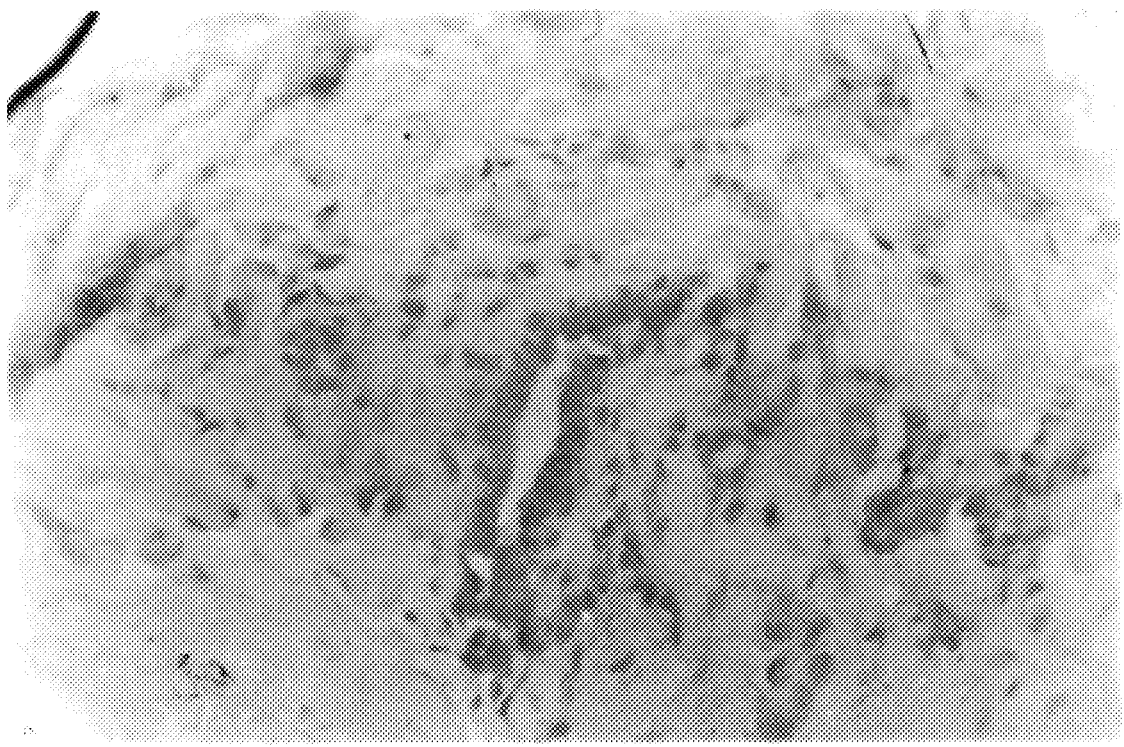
Figure 7B:
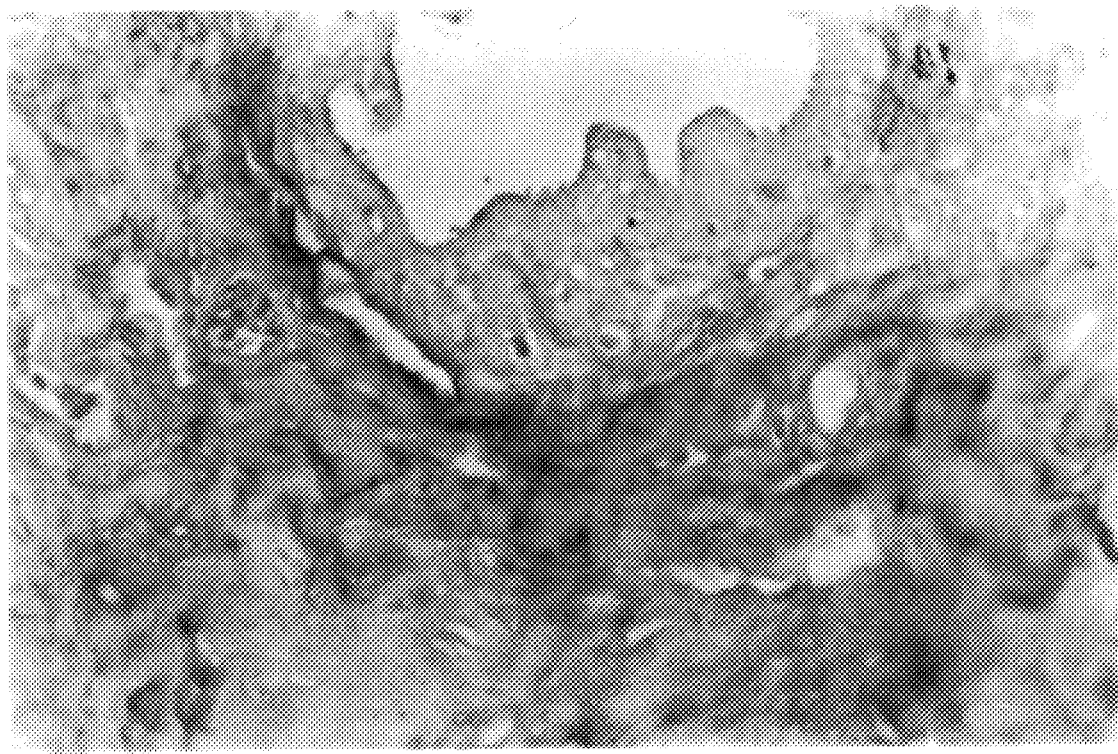

FIGS. 7A and 7B are color photographs comparing the breast cancer near adjacent tissue (NAT) with tissue from a normal breast stained for 16OHE1-glucuronide fraction according to the APAAP direct immunocytochemical assay method of this invention. The breast tumor (NAT) tissue (Patient 7893) demonstrates bright red staining surrounding the ductal elements, whereas the normal tissue of similar structure (Patient Co37) is totally unstained. Photographs ere taken at 845× magnification.

Figure 8:
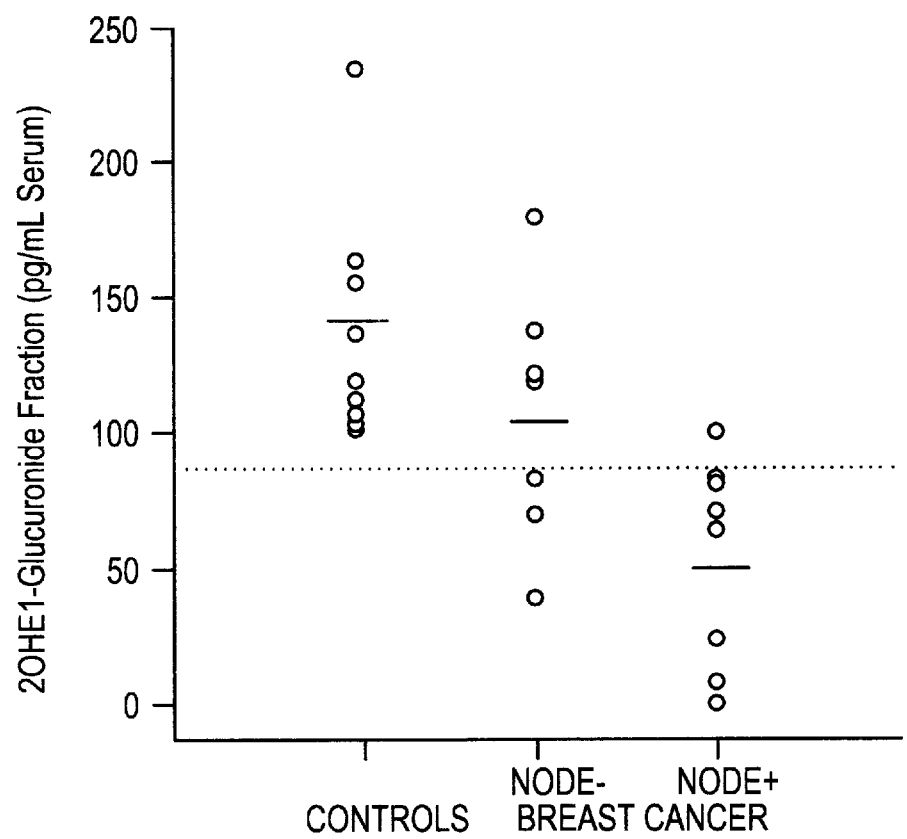
Figure 9A:
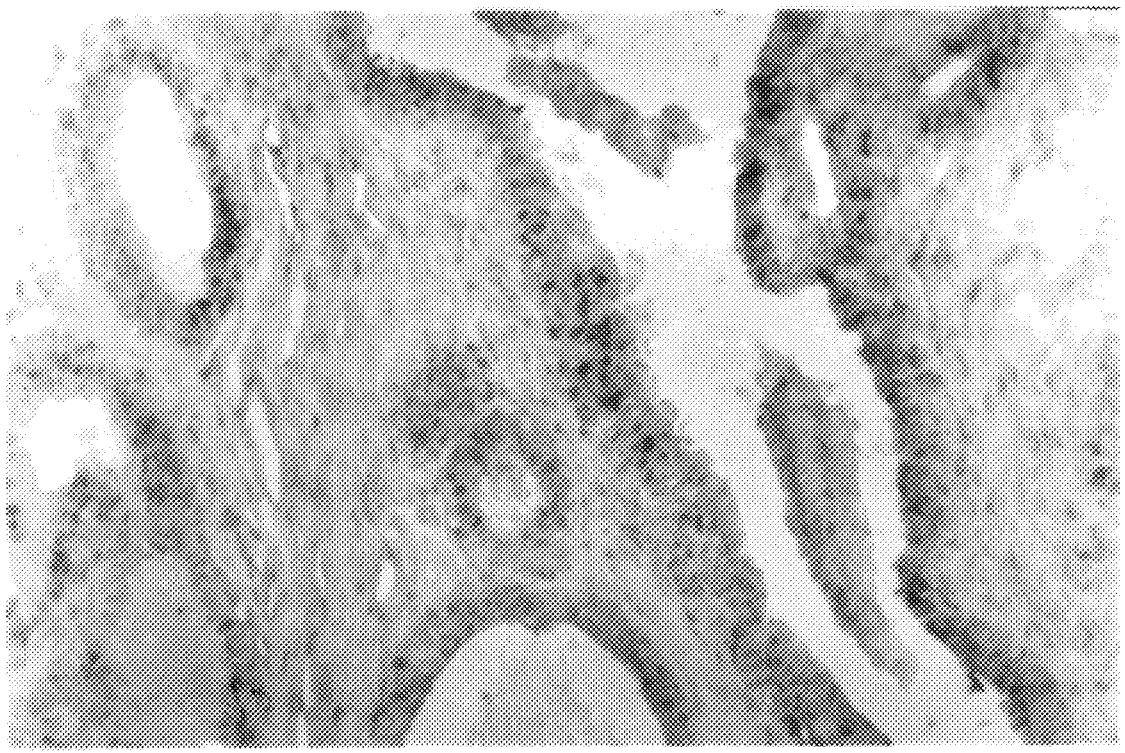
Figure 9B:

FIG. 8 is a graph comparing the levels of the 2OHE1-glucuronide fraction in sera of healthy women to those of women with both node-negative and node-positive breast cancer, FIGS. 9A and 9B are color photographs comparing the breast cancer tissue with tissue taken from a normal breast stained for 2OHE1-glucuronide fraction according to the APAAP direct immunocytochemical assay method of this invention. The breast tumor tissue (Patient 7940) demonstrates purple (red plus blue) staining nuclei of only one apparently normal ductal element within the tumor, whereas the normal tissue of similar structure (Patient Co78) has stained nuclei within all of the cells. Photographs were taken at 845× magnification.

Figure 10:
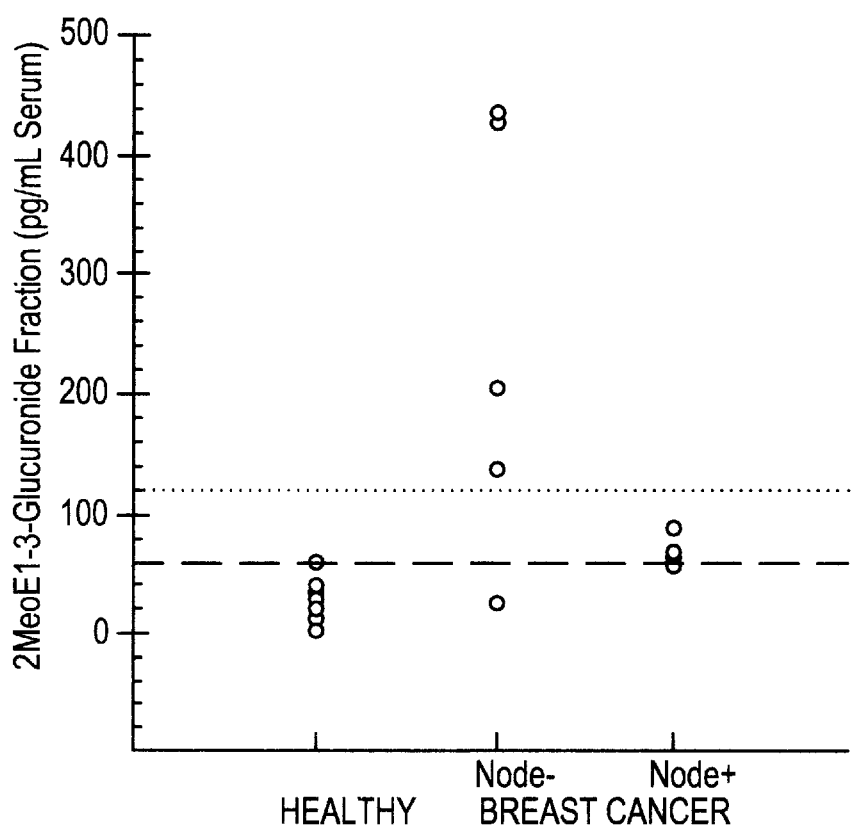

FIG. 10 is a graph comparing the levels of the 2MeoE1-glucuronide fraction in sera of healthy women to those of women with both node-negative and node-positive breast cancer.

Figure 11:
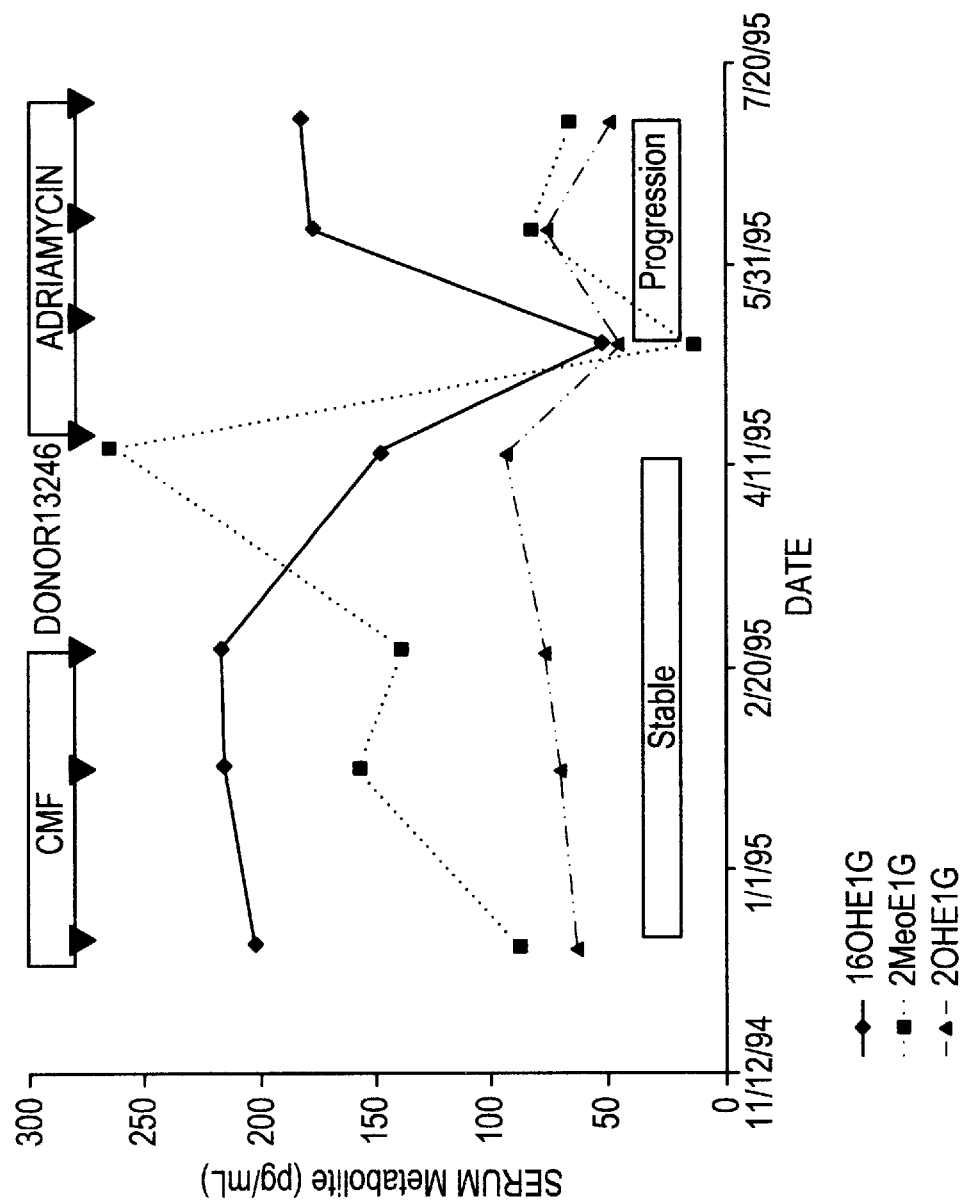

FIG. 11 is a graph illustrating the serial monitoring of chemotherapeutic treatment of a 76 year old woman with advanced breast cancer (stage III) with ELISAs for 2OHE1-, 2MeoE1-, and 16OHE1-glucuronide fractions in serum.

FIG. 12 is a graph which further demonstrates the longitudinal monitoring of chemotherapy of a 77 year old woman with metastatic breast cancer (stage IV) with ELISAs for serum 2OHE1-, 2MeoE1-, and 16OHE1-glucuronide fractions.

DESCRIPTION OF THE INVENTION

While not wishing to be bound by any particular theory, it is believed that previous methods to detect and/or quantify estrogen metabolites such as 16OHE1, as by immunological assays, have failed because investigators did not recognize that such metabolites, and especially 2OHE1, 2MeoE1, and 16OHE1 in tissues and bodily fluids exist predominantly in the form of glucuronides rather than as free, unconjugated species. Moreover, it was not known that it is the glucuronide fraction (free plus 3-glucuronide) that is altered most significantly in animals bearing malignant tumors. Further, investigators did not recognize that the physical-chemical nature of the estrone metabolite glucuronide, that is, its negative charge and ability to form Schiff's bases with amines, promote sequestration of glucuronide in tissues and bodily fluids, chiefly within protein. Therefore, immunological assays would not be able to detect and/or quantify the glucuronide fraction in tissues and body fluids unless the assays are done under specific conditions adopted to liberate the tightly bound glucuronide fraction, and high affinity, high specificity antibodies that recognize the glucuronide fraction are used.

The present invention overcomes the limitations of the prior art by utilizing in the practice of this invention antibodies which recognize epitopes on both the free estrone metabolite and its 3-glucuronide conjugate equivalently, thus providing assays that are able to simultaneously detect and/or quantify both the unconjugated and 3-glucuronide forms of the estrone metabolite. The novel buffer compositions, monoclonal antibodies, and assay methods taught herein enable nearly complete recovery of sequestered 2OHE1, 2MeoE1, 16OHE1 and their respective 3-glucuronides from tissues and bodily fluids with antibodies of this invention.

The Examples section illustrates the use of the 2OHE1-, 2MeoE1, and 16OHE1 glucuronide fractions in screening methods for use as tumor markers and tumor-associated antigens.

The diagnostic/prognostic methods illustrated herein can be used for the detection of neoplastic disease. Also provided are compositions and test kits for implementing such methods. The discovery that said estrone metabolite glucuronide fraction is altered in human tissues and serum of cancer patients has opened the way for the development of novel methods and compositions for the diagnosis and treatment of malignant disease in humans and other mammals. The assays of this invention are both diagnostic and/or prognostic. The term "diagnostic/prognostic" is herein defined to encompass the following processes depending upon the clinical context: determining the presence, extent, and nature of the disease; differentiating benign from malignant disease; predicting the most likely course and outcome of the disease; monitoring a patient for recurrence of disease; and, determining the preferred type and timing of therapy for a patient with cancer.

In a highly preferred embodiment of the invention, the screening method disclosed herein utilizes the detection of 16OHE1 and its conjugates at elevated levels in tissues and in bodily fluids of mammals to determine which carry a malignant tumor. The elevated portion of 16OHE1 in serum comprises substantially 16OHE1-3-glucuronide and 16OHE1, termed the "16OHE1-glucuronide fraction", and the detection and measurement of this fraction provides highly useful methods for detecting the presence and extent of tumors in neoplastic disease, particularly in breast cancer.

Similarly, in a highly preferred embodiment, the screening method disclosed herein utilizes the detection of 2OHE1 glucuronide fraction and/or 2MeoE1 glucuronide fraction at relatively high, moderate, or low levels in tissues and body fluids of mammals bearing a tumor burden, or to predict the liklehood of tumor regression, stability, or progression of an estrogen-sensitive neoplastic disease, particularly in breast cancer.

Methods and compositions are provided for detecting and/or quantifying said 2OHE1-, 2MeoE1-, and 16OHE1-glucuronide fractions in tissues and bodily fluids. Further, diagnostic/prognostic methods are provided wherein other conjugated fractions of 2OHE1, 2MeoE1, and 16OHE1 are found in mammalian bodily fluids. For example, specific glycolytic and/or arylsulpholytic enzymes may be used to convert conjugates of 16OHE1 including 16OHBE1-3,16-glucuronide, 16OHE1-16-glucuronide, 16OHE1-3-sulphate, and 16OHE1-3-sulphate-16-glucuronide to unconjugated 16OHE1 or 16OHE1-3-glucuronide for assay in the described immunoassays of this invention.

Figure 1:
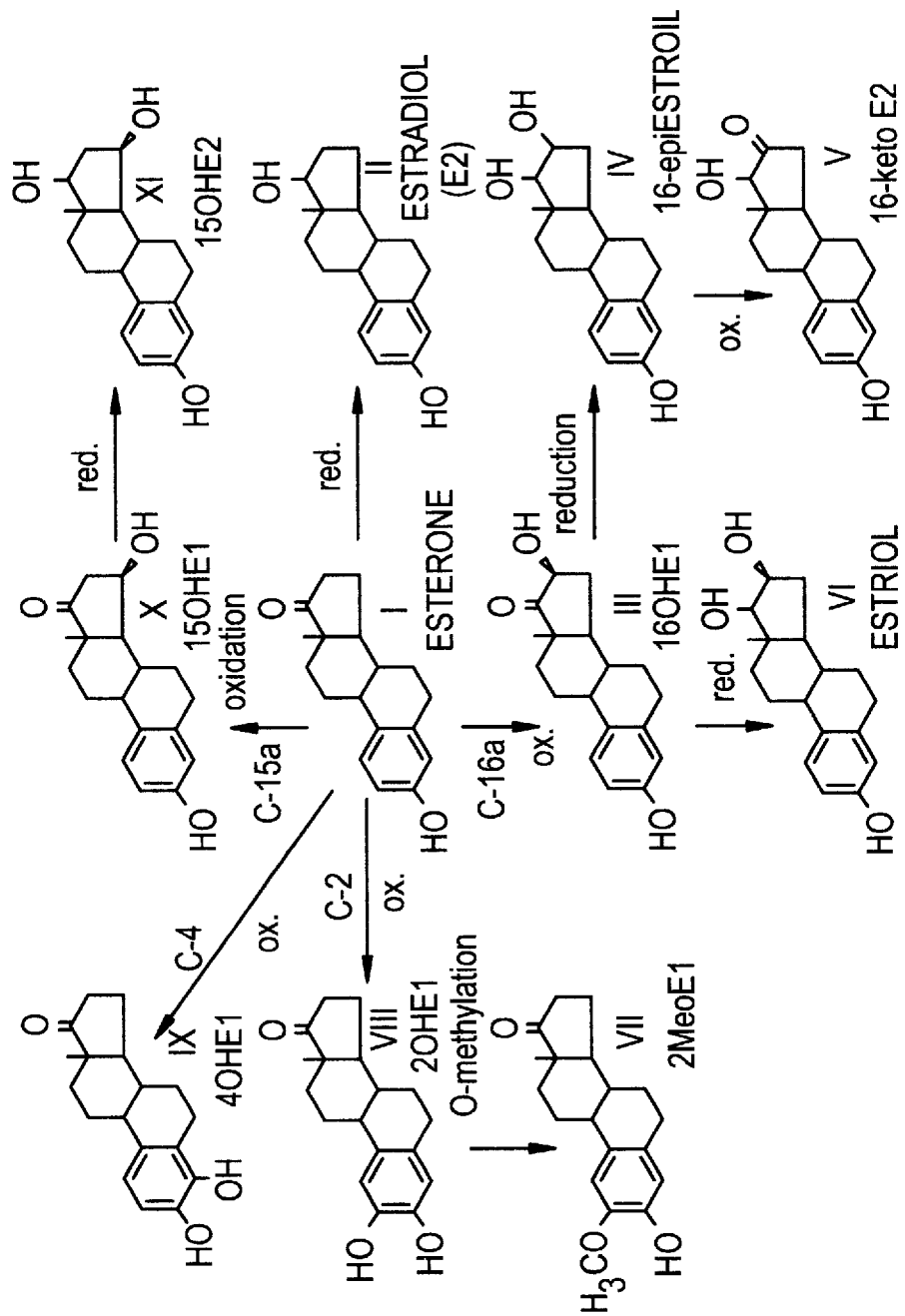
FIG. 1 is a chart illustrating the principal oxidative and reductive metabolites of estrone.
Figure 2:
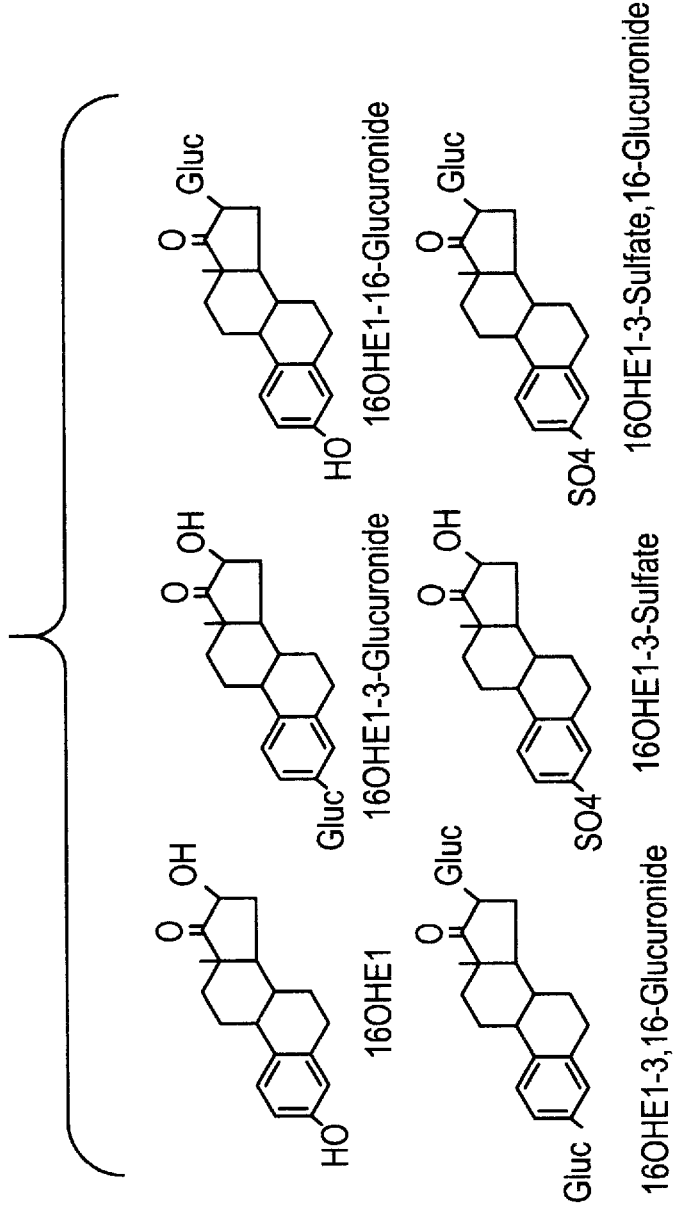
FIG. 2 is a chart showing the hypothetical conjugates of 16OHE1 as they might occur in tissues and/or body fluids of humans, and other mammals.

"Substantially" as used in the context of the "glucuronide fraction" indicates that although the estrone metabolite and its glucuronide and sulphate conjugates are elevated in malignant tissues, the significant, variable fraction of conjugated estrone metabolites in tissues and body fluids of mammals bearing malignant tumors exists as the 3-glucuronide. It can be appreciated that an estrogen within the bodily fluids would be subject to a variety of metabolic processes, including glucuronidation and sulphation, among others. Further, it can be appreciated that cells within tissues under the influence of neoplastic processes might conjugate estrogens differently than cells within normal healthy tissues. Thus, by way of illustration, not limitation, the "16OHE1-glucuronide fraction" would encompass 16OHE1 and 16OHE1-3-glucuronides, as well as 16OHE1 conjugated at the 3-position with chemical moieties other than glucuronides (FIG. 2). Assays according to the present invention would detect and/or quantify 3-substituted 16OHE1, if the 3-substituent were a small sugar, an amino acid, or other neutral or charged compound. The said 16OHE1-glucuronide fraction includes unconjugated 16OHE1 because a portion of 16OHE1-3-glucuronides may be converted to 16OHE1 by hydrolysis during isolation and/or processing of tissues or body fluids, as by endogenous β-glucuronidases or chemical treatments.

Representative methods and compositions according to this invention include those for identifying patients who have a pathology associated with an alteration in estrogen metabolism, especially a neoplastic disease, and most especially, malignant tumors. An exemplary method comprises the steps of detecting the level of the said 16OHE1-glucuronide fraction as described herein in a sample of patient's tissue or bodily fluid, and determining whether that level is elevated above normal. As shown herein, malignant tumors and tissues adjacent to malignant tumors release higher levels of said 16OHE1-glucuronide fraction into bodily fluids than do benign tumors or normal tissues. Thus, a higher level than normal level of said 16OHE1-glucuronide fraction is indicative of the presence of one or more malignant tumors. Conversely, due to the metabolic processes by which they are derived, and their antiestrogenic activities, an altered level of the 2OHE1- or 2MeoE1-glucuronide fraction in tissues and body fluids of a mammal bearing a tumor burden, or suspected of bearing a tumor, may be indicative of the presence of one or more malignant tumors, or be prognostic for progression or regression of an estrogen-sensitive malignancy, especially breast cancer.

In the practice of this invention the animal tested is preferably human, and the bodily fluid tested is preferably serum. An important parameter of the status and likely outcome of the patient with gynecologic cancer can be determined by testing a body fluid, preferably serum, from the patient for elevated 16OHE1-glucuronide fraction. Exemplary means of detecting and/or quantifying said 16OHE1-glucuronide fraction, whether in mammalian body fluids, tissues or tissue extracts, include ligand binding assays, and immunoassays among other means.

Immunoassays are the preferred means of detecting the 2OHE1-, 2MeoE1, or 16OHE1-glucuronide fractions, most preferably, a competitive inhibition immunoassay. In such an immunoassay format, antibodies specific to said 16OHE1-glucuronide fraction, 2MeoE1-glucuronide fraction, or 2OHE1 -glucuronide fraction can be used with their paired respective 16OHE1-labeled, 2MeoE1-labeled, or 2OHE1-labeled enzymes, radioisotopes, fluorescent, or chemiluminescent tracers to compete with estrogen metabolite for binding to antibodies. Such antibodies can be prepared by methods known in the art, and described, for instance, in Klug et al., Steroids, Vol. 59, pp. 648–655 (1994).

An important parameter of the status and likely outcome of the patient with gynecologic cancer can be determined by testing tissue, preferably fresh or formalin-fixed paraffin-embedded tissue sections. Exemplary means of detecting and/or quantifying said 2OHE1- or 16OHE1-glucuronide fraction in tissues include immunohistochemical detection, preferably with the alkaline phosphatase-antialkaline phosphatase (APAAP) method.

Further, assay results obtained according to the practice of this invention indicating the presence of abnormal levels of glucuronide fraction in body fluids or tissues of humans can be used in conjunction with results of other assays of neoplastic disease, such as, for example, estrogen receptor (ER) and progesterone receptor (PR) assays, to provide useful prognostic and diagnostic information.

Still further, the assays of this invention are useful for detection of malignant disease both pre- and post-operatively. For example, patients displaying elevated levels of said 16OHE1-glucuronide fraction in early stages of disease may be treated more aggressively, thus affording the patient a chance of increased survival. By contrast, patients with early stage tumors, or even relatively advanced tumors with low, normal, or slightly elevated 16OHE1-glucuronide fraction may be treated more conservatively, thus avoiding chemotherapeutic trauma and excess costs. Similarly, increases or decreases in said 16OHE1-glucuronide fraction during therapy may correlate with, and corroborate, objective evidence of the patient's response to therapy. The levels of 2OHE1- and/or 2MeoE1-glucuronide fraction can be similarly utilized.

The assays of this invention can also be used to predict the likely existence of lymphatic involvement (nodal status) and/or metastatic spreads of malignant disease. For example, patients displaying very elevated levels of said 16OHE1-glucuronide fraction and low levels of 2OHE1 and/or 2MeoE1-glucuronide fraction, may be considered to have, or be at increased risk, of lymphatic involvement and metastatic spread of disease. This information may be used in conjunction with other available information to more accurately stage the cancer, and decide upon the course and timing of treatment.

The assays of this invention which indicate the presence of said glucuronide fraction in body fluids of humans are useful to detect and diagnose cancer, including screening of populations for cancer, preferably when used adjunctively with other screening methods such as mammography and cervical PAP testing.

The invention also provides for test kits useful for the practice of the assays of the invention wherein said test kits comprise antibodies reactive with 2OHE1, 2MeoE1, 16OHE1 and/or said 2OHE1-, 2MeoE1-, and 16OHE1-glucuronide fractions, enzymes, radioisotopes, fluorescers, or chemiluminescers as detection elements, in combination with containers, pipettes, slides, plate, coated well, etc., typically utilized in such test kits. The assays can be solid phase assays, but are not limited thereto, and can be in a liquid phase format, and can be based on enzyme-linked immunosorbent assays (ELISAs), radioimmunoassays, fluorometric assays, chemiluminescent assays, and particle agglutination assays, all of which may be amplified or unamplified through methods known in the diagnostic arts.

The concept underlying this invention is the discovery that patients suffering from a pathology associated with an alteration in estrogen metabolism have in their bodily fluids abnormal levels of metabolites of estrone, and the altered fraction of estrone metabolites associated with the pathology is, in a preferred embodiment, substantially the sum of the metabolite-3-glucuronide and unconjugated metabolite, herein designated the "glucuronide fraction". The said glucuronide fraction may thus be utilized as a novel tumor marker and tumor-associated antigen.

Assays for Glucuronide Fraction in Mammalian Tissues and Body Fluids

Figure 3:
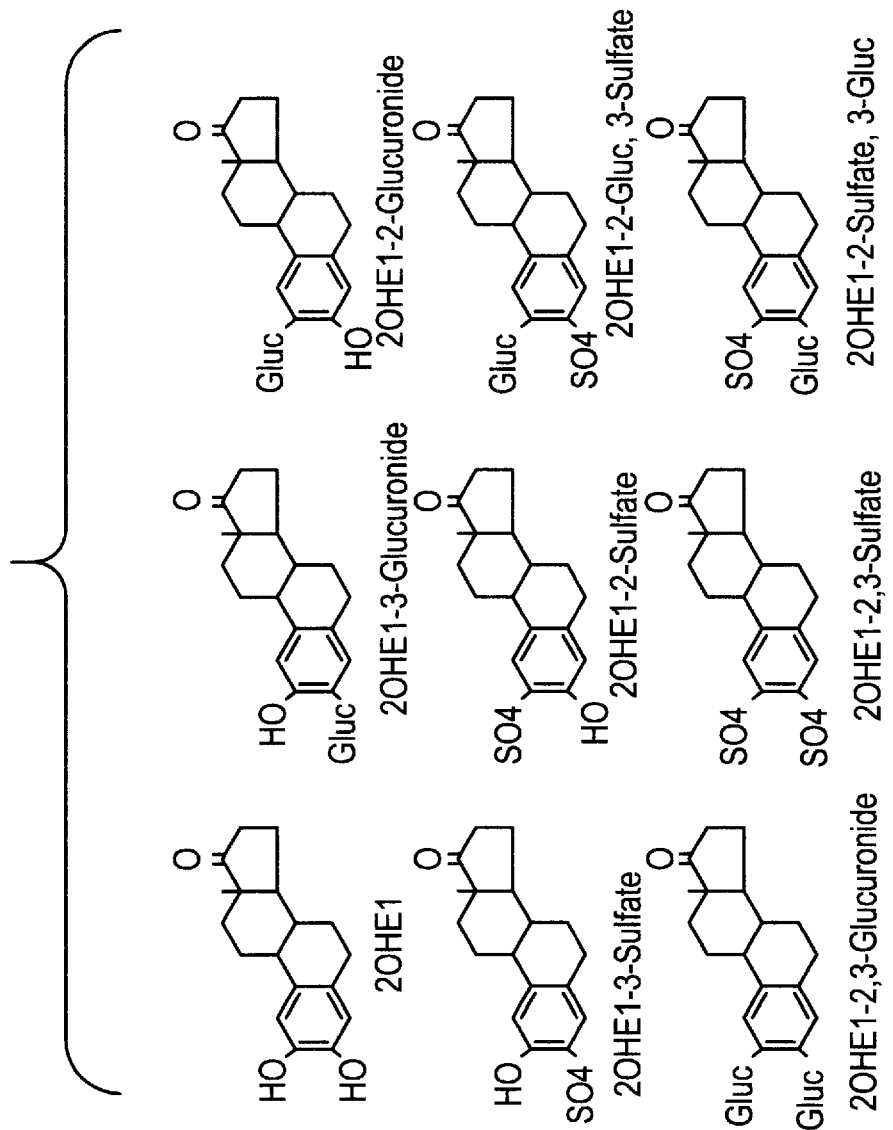
FIG. 3 is a chart showing the hypothetical conjugates of 2OHE1 as they might occur in tissues and/or body fluids of humans, and other mammals.
Figure 4:
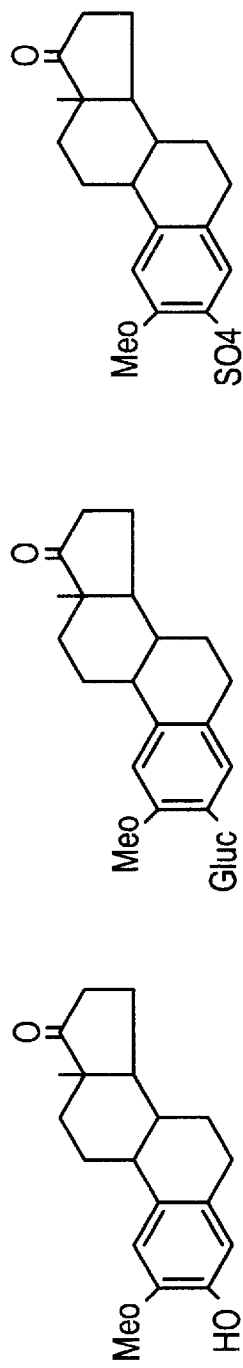
FIG. 4 is a chart showing the hypothetical conjugates of 2MeoE1 as they might occur in tissues and/or body fluids of humans, and other mammals.

Non-invasive diagnostic/prognostic assays are provided to detect and/or quantify said glucuronide fraction in body fluids of mammals, preferably humans. It can be appreciated that metabolites of estrone may be present in a patient's tissues and body fluids as, in the case of 16OHE1, unconjugated metabolite, metabolite-3-glucuronide, metabolite-3, 16-glucuronide, metabolite-16-glucuronide, metabolite-3-sulfate, or metabolite-3-sulfate, 16-glucuronide conjugates, among others (see FIG. 2). Said conjugates may be detected and/or quantified by the assays of this invention if they contain epitopes recognized by the antibodies of this invention. Certain conjugates of estrone metabolites may require pretreatment with enzymes prior to assay to remove conjugated groups that obscure the epitopes recognized by the antibodies of this invention. For example, treatment of 16OHE1-3,16 -glucuronide with the enzyme β-glucuronidase, preferably enzyme derived from *E. Coli*, will reduce the former conjugate to 16OHE1 or 16OHE1-3-glucuronide, both recognized equally by antibodies of this invention. Treatment of 16OHE1-3-sulfate with the enzyme arylsulfatase, preferably that derived from the snail, Helix Pomatia, will reduce the former conjugate to 16OHE1, an estrogen recognized by antibodies of the present invention. Treatment of the mixed conjugate 16OHE1-3-sulfate, 16-glucuronide with a mixture of the enzymes β-glucuronidase and arylsulfatase described, will reduce the former 16OHE1 conjugate to 16OHE1. The exact use of these same enzymes with conjugates of 2OHE1 and 2MeoE1 (FIGS. 3 and 4) to obtain unconjugated and partially conjugated forms of 2OHE1 and 2MeoE1 is obvious to those skilled in the art.

The body fluids that are of particular interest in assaying for said glucuronide fraction according to methods of this invention include blood, serum, plasma, urine, breast exudate, saliva, sputum, cytosols, ascites, pleural effusions, and cerebrospinal fluid. Blood, serum, and plasma are preferred, and serum is the most preferred body fluid according to methods of this invention. The assays of this invention can also be used to detect and/or quantify the glucuronide fraction in tissues. Tissue preparations of particular interest include fresh tissue sections, fixed paraffin-embedded tissue sections, cell smears, cell suspensions, or freeze-mounted cells, preferably formalin-fixed paraffin-embedded tissue sections.

From a knowledge of the conjugates associated with malignant diseases, said glucuronide fraction as disclosed in this invention, monoclonal or polyclonal antibodies can be generated that specifically recognize said glucuronide fraction, that is, 16OHE1 and 16OHE1-3-glucuronide, 2OHE1 and 2OHE1-3-glucuronide, and 2MeoE1 and 2MeoE1-3-glucuronide. Because the said glucuronide fraction is found to be tightly bound to proteins, said fraction is not ordinarily found to exist freely in the tissues and body fluids of mammals. By methods revealed in this invention, however, said glucuronide fraction may be sufficiently liberated for binding by antibodies of this invention making detection and/or quantification possible. Utilizing current immunodiagnostic techniques that can quantify the binding of said glucuronide fraction to monoclonal antibodies of this invention, one can determine the amount of said 16OHE1-glucuronide fraction in tissues and body fluids of cancer patients. Representative immunoassays involve the use of monoclonal antibodies and estrone metabolite-enzyme conjugates in competitive enzyme-linked immunoassays (ELISAs).

A preferred method to generate monoclonal antibodies involves covalently linking a metabolite, such as 2OHE1, 2MeoE1, or 16OHE1 to a protein and using it as an immunogen. Still further, the metabolite-glucuronide, such as 2OHE1-, 2MeoE1-, or 16OHE1-3-glucuronide, can be covalently linked to protein and be used as antigen. By this method, many monoclonal antibodies recognizing and binding different conjugates of 16OHE1 or other estrone metabolites can be generated and selected, and such antibodies could be used to detect or identify differently conjugated fractions of 16OHE1 or other metabolites of estrone. The monoclonal antibodies of this invention were generated in mice after immunization with 2OHE1, 2MeoE1, or 16OHE1 covalently linked to keyhole limpet hemocyanin (KLH), and individual antibodies were selected to recognize and bind both the unconjugated metabolite and its respective-3-glucuronide with high affinity and specificity.

The diagnostic/prognostic assays with monoclonal antibodies according to this invention would typically involve obtaining a small amount of body fluid, preferably serum, from the mammalian host. The presence of the particular metabolite glucuronide fraction in serum can then be detected and/or quantified by a variety of immunodiagnostic techniques, including ELISA, RIA, and fluorescent. chemiluminescent assays, among others. For example, a representative of one type of ELISA test is a format wherein a microtiter plate is coated with, for example, monoclonal antibody to 16OHE1/16OHE1-3-glucuronide, and to said microtiter plate is added an appropriately treated sample of patient serum mixed with an enzyme covalently labeled with 16OHE1. After a period of incubation permitting competition between 16OHE1-enzyme and serum 16OHE1-glucuronide fraction for binding to monoclonal antibody bound to the solid phase, the plate is washed, and a color-generating enzyme substrate is added to determine the amount of 16OHE1-enzyme bound. The quantity of 16OHE1-glucuronide fraction in each serum sample is determined from the absorbance of the sample relative to a set of 16OHE1-glucuronide standards and controls of known concentration. The amount of inhibition of absorbance is directly proportional to the concentration of said 16OHE1-glucuronide fraction in each serum sample. It is apparent to one skilled in the art of diagnostic/prognostic assays that a wide variety of immunological assay methods are available for measuring the formation of antigen antibody complexes. Numerous formats and protocols for immunodiagnostic assays are described in the scientific and patent literature. Exemplary immunoassays which are especially suitable for detecting a serum antigen include those described in U.S. Pat. Nos. 3,654,090, 3,850,752, RE U.S. Pat. Nos. 31,006 and 4,016,043. Antibodies employed in assays may be labeled or unlabeled. Suitable detection means include the use of labels such as enzymes, radioisotopes, fluorescers, chemiluminescers, particles, dyes, and the like. Such labeled reagents may be used in a variety of well known assay formats. See, for example, U.S. Pat. Nos. 3,654,090, 3,850, 752 and 4,016,043.

The assays of the present invention are useful for screening for a wide variety of neoplastic diseases wherein an elevation or change in estrogen metabolism is indicative of disease or a susceptibility thereto. Exemplary neoplastic diseases include carcinomas, such as adenocarcinomas, melanomas, squamous cell carcinomas, mesodermal tumors, sarcomas, leukemias, and lymphomas. Of particular interest are gynecological cancers including ovarian, cervical, vaginal, endometrial, and breast cancer. Tumors of tissues which are known to express estrogen receptors (ER) are good candidates for neoplastic diseases for use of assays of this invention. As outlined in the Background above, increased 16α-hydroxylation has been associated with breast, cervical, and endometrial cancer in mammals, and, therefore, the assays of this invention are especially useful in the screening for and monitoring of these cancers.

Competitive Direct Enzyme-linked Immunoassay

A preferred assay format for the glucuronide fraction according to this invention is the competitive enzyme-linked immunoassay. Briefly, the concentration of the glucuronide fraction is determined by competitive binding between the glucuronide fraction in body fluids and metabolite-labeled enzyme for antibody to glucuronide fraction bound to a microtiter plate. Antibody bound to the solid phase provides a capture system for said glucuronide fraction, estrone metabolite-labeled enzyme. Higher concentrations of said glucuronide fraction in solution competitively inhibits binding of metabolite-labeled enzyme, and after equilibrium is reached, the amount of enzyme captured by antibody on the solid phase is determined by adding a colorless enzyme substrate which becomes colored after reacting with enzyme on the solid phase. The amount of glucuronide fraction is determined by reference to standards containing known amounts of the metabolite-3-glucuronide. A further competitive ELISA according to this invention reverses the orientation of antigen and antibody in the assay, wherein glucuronide fraction covalently coupled to protein is bound to the solid phase and antibody to said glucuronide fraction is labeled with enzymes.

There are many different embodiments of the competitive inhibition ELISA. For example, In a preferred format for 2OJHE1, 2MeoE1, or 16OHE1 glucuronide fractions, rabbit antibody to mouse IgG, Fc-fragment specific (Jackson ImmunoResearch, Avondale, Pa., U.S.A.) Maxisorb 8×12 plate, NUNC, U.S.A.), wherein the coating volume is 150 uL/Ml, and the antibody concentration is 2 ug/Ml in PBS. In such a preferred assay, bodily fluid diluted in an appropriate buffer is mixed in solution with a monoclonal antibody to said 16OHE1-glucuronide fraction, preferably the monoclonal antibody clone 19H7 (described below), and 16OHE1-labeled enzyme, preferably 16OHE1-alkaline phosphatase (AP, Sigma Chemical Co., St. Louis, Mo. U.S.A.). It is preferred that there be 5–10 ng/mL of monoclonal antibody, and 0.5–1 U/mL of 16OHE1-labeled AP in a reaction volume of 150 uL. It is preferred that body fluid, preferably serum be diluted 1:4 to 1:20 in the assays of this invention.

It is preferred that 16OHE1 derivatives for conjugation to enzymes and other proteins be synthesized as described by Ikegawa and Fishman, Steroids, 39:557–567, 1982, and be linked to enzyme, preferably AP, following Mattox, Litwiller, and Nelson in J. Steroid Biochem. 10:167–172, 1979. A preferred method for preparing estrone metabolite-3-glucuronide and estrone metabolite-3-glucuronide-labeled enzymes and proteins for use according to this invention is isolation from late pregnancy urine and conjugation to enzymes and proteins as described by Samarajeewa, Leepipatpaiboon, and Coulson, Steroids 36:611–618, 1980.

Preferred hydrogen ion buffers for assays of this invention are those commonly known as "Good" buffers as described by Good et al. in Biochemistry 5: 467–477, 1966, and in Analytical Biochemistry 104:300–310, 1980. These buffers are typically zwitterionic amino acids, either N-substituted taurines or N-substituted glycines, and are preferred because these compounds assist in disrupting the interactions between the said glucuronide fraction and proteins in tissues and body fluids. These buffer salts achieve this effect through ion-pair formation with the negatively charged glucuronides, and by their amphiphilic nature, promote the base catalyzed hydrolysis of Schiff's bases between said 16OHE1-glucuronide fraction and primary amino groups on proteins. Further, it is preferred that the buffers of assays of this invention be kept acidic (pH<7.0) to protonate said 16OHE1-glucuronide fraction, thereby minimizing charge interactions with proteins in tissues and body fluids. Assays described in this invention utilize the Good buffer 2-(N-Morpholino) ethanesulfonic acid (MES).

It is further preferred that assays of this invention be performed at temperatures below 15 deg. Centrigrade.

Example 1 below provides the details of a preferred protocol for a competitive direct ELISA to detect and/or quantify the said 16OHE1-glucuronide fraction in serum according to this invention. Further, Example 2 below provides details of a protocol to detect and/or quantify total serum 16OHE1-glucuronides. Example 4 below provides the details of a preferred protocol for a competitive ELISA to detect and/or quantify the said 2OHE1-glucuronide fraction in serum according to this invention. Example 6 below provides the details of a preferred protocol for a competitive ELISA to detect0 and/or quantify the said 2MeoE1-glucuronide fraction in serum according to this invention.

Immunocytochemical assays

A preferred assay method for the detection and/or quantification of said glucuronide fraction in tissues according to this invention is the immunoenzymatic labeling procedure utilizing the "unlabeled antibody bridge", preferably the alkaline phosphatase:anti-alkaline phosphatase (APAAP) technique, and fixed tissue sections, preferably formalin-fixed paraffin-embedded tissue sections. In this method, prepared glass slide mounted tissue sections are incubated sequentially with: 1) mouse monoclonal antibody to said glucuronide fraction; 2) rabbit polyclonal anti-mouse IgG antiserum: and 3) mouse anti-alkaline phosphatase:alkaline phosphatase immune complexes (APAAP). The rabbit anti-mouse IgG acts to bridge the primary monoclonal antibody the APAAP complex, linking the two together. The presence of tissue-bound APAAP, and hence tissue-bound antibody to the said glucuronide fraction, is visualized by incubation of the treated tissue with a color producing substrate for alkaline phosphatase, preferably napthol AS-MX as coupling reagent and Fast Red as capture agent yielding a bright red color. There are many different embodiments of the immunoenzymatic "unlabeled antibody bridge" technique including those using the peroxidase:antiperoxidase (PAP) technique.

In a preferred format for said glucuronide fraction, glass slide mounted formalin-fixed paraffin-embedded sections, preferably 4 to 10 um thick, are deparaffinized with n-decane, rehydrated, and incubated with monoclonal antibody to said glucuronide fraction in TBS. The tissue is washed extensively with TBS, incubated for 1 hour with rabbit antibody to mouse IgG, is washed with TBS, and incubated with APAAP complex for 30 min. After a final wash with TBS, bound primary monoclonal antibody to said 16OHE1-glucuronide fraction is detected and/or quantified by incubating with a mixture of napthol AS-MX and Fast Red in diethanolamine buffer, pH 8.9, for about 10 minutes, or until intense red color is produced. Levamisole (5 mM) is included in the substrate buffer to inhibit endogenous alkaline phosphatase activity in tissues. Commercial APAAP kits containing reagents for use with murine monoclonal antibodies are available for the described procedure, preferably that manufactured by DAKO Corporation, Carpenteria, Calif. U.S.A. (Product No 670K). The concentrations of all reagents are adjusted to optimize development of specific staining, while keeping non-specific background staining to a minimum. General techniques and principles of immuno-tabeling of monoclonal antibodies by the APAAP technique are discussed further by Mason in *Techniques in Immunocytochemistry*, Vol. 3, pp. 25–42, Bullock and Petrusz, eds., Academic Press, 1985. Example 3 below provides details of a preferred protocol for an immunocytochemical immunoenzymatic APAAP assay for said 16OHE1-glucuronide fraction according to this invention. Example 5 below provides details of a preferred protocol for immunocytochemistry of 2OHE1-glucuronide fraction in tissues.

Test Kits

The above assay according to this invention can be embodied in test kits to detect and/or quantify the estrogen metabolite-glucuronide fraction in mammalian, preferably human, tissues and body fluids wherein such test kits comprise antibodies, monoclonal and/or polyclonal, that can recognize epitopes on the estrogen metabolite-glucuronide fraction. Such diagnostic/prognostic kits, for instance in the case of 16OHE1, can further comprise, alone or in combination with the aforementioned antibodies to said 16OHE1-glucuronide fraction, labeled 16OHE1 and/or labeled 16OHE1-3-glucuronide, 16OHE1 and/or 16OHE1-3-glucuronide standards dispersed in tissues or body fluids, as well as positive and/or negative controls, and other reagents as necessary to perform the assays according to this invention. Example 7 below provides a detailed description of one such test kit for the measurement of the 16OHE1-glucuronide fraction in human serum. Example 8 below provides a detailed description of one such test kit for the measurement of the 16OHE1-glucuronide fraction in human tissues. It is obvious to those skilled in the art, given the Examples, that similar kits for 2OHE1 and 2MeoE1 glucuronide fraction may be readily constructed.

Preparation of Monoclonal Antibodies

Monoclonal antibodies useful in this invention are obtained by the well-established process of cell fusion as described by Milstein and Kohler in Nature 256:495–497, 1975, and, more preferably, for antibodies to said 16OHE1-glucuronide fraction and 16OHE1-3-glucuronide for assays according to this invention, as described by Lane, Crissman, and Ginn in Methods of Enzymology 121:183–192, 1986.

MAbs 12C2, 12D7, 16F11, and 19H7 to 16OHE1-glucuronide Fraction

All monoclonal antibodies were made by fusing splenocytes from female Balb/C mice immunized with 16OHE1-KLH estrogen:protein conjugates with non-immunoglobulin secreting murine myeloma cell line SP2/O-AG14 (ATCC CRL1581). It is preferred that 16OHE1 derivatives for conjugation to enzymes and other proteins be synthesized as described by Ikegawa and Fishman in Steroids 39:557–567, 1982, and be linked to protein following Mattox, Litwiller, and Nelson in J. Steroid Biochem. 10:167–172, 1979. A preferred method for preparing 16OHE1-3-glucuronide and 16OHE1-3-glucuronide-labeled enzymes and proteins for use according to this invention is isolation from late pregnancy urine and conjugation to enzymes and proteins as described by Samarajeewa, Leepipatpaiboon, and Coulson in Steroids 36:611–618, 1980.

Six 10–14 week old female Balb/C mice were immunized i.p. with 50–100 ug of 16OHE1-KLH conjugate in 0.5 mnL of TiterMax adjuvant (CytRx Corporation, Norcross Ga. U.S.A.) in PBS (50:50 v/v). Animals were boosted i.p. with 50–100 ug of emulsified antigen in TiterMax at monthly intervals for three months, or until mice demonstrated antibody to conjugate. Mice were bled and tested for antibody to 16OHE1/16OHE1-3-glucuronide every two weeks in an ELISA (described below). Mice with highest titers were injected intravenously with 100 ug of 16OHE1-KLH in sterile saline via the tail vein 4 days prior to cell fusion. Splenocytes from boosted mice were fused with SP2/O-AG14 mouse myeloma fusion partner cells using the high efficiency fusion protocol described by Lane, Crissman, and Ginn (see reference above). Spleen cells at 5:1 ratio with SP2/O cells were fused with 30% polyethylene glycol 1000, and distributed in 0.13 mL aliquots into twenty-five 96-well culture plates at $4 \times 10^4$ cell per well in media containing Hybridoma Enhancing Medium (HEM, Sigma Chemical Company, St. Louis, Mo. U.S.A.). A super-rich growth medium consisting of HY medium (90% DMEM, high glucose, 10% NCTC 135), 20% fetal bovine serum, 4 Mm L-glutamine, 20% HEM, and 30 ug.Ml carboxyethyl gama-amino butyric acid (GABA) was used for feeding and subcloning. Selection for hybridoma cells was with hypoxanthine and azaserine. Each well was tested for antibody to 16OHE1/16OHE1-3-glucuronide when it became confluent with hybrid cells. All of the wells were tested over a three week period, and positive hydrids were cloned twice by limiting dilution in super rich medium without azaserine.

The presence of antibodies to 16OHE1-glucuronide fraction and/or 16OHE1-3-glucuronide was determined by a specific ELISA. Microtiter plates were coated 16 hours with rabbit anti-mouse IgG in PBS. The plates were blocked with 1% BSA in PBS for 1 hour, and after washing, culture supernatants (100 uL/well) were added to the plates and incubated for 2 hours. Plates were washed, and 16OHE1-alkaline phosphatase (300 U/mL) diluted 1:2000 with 0.1% gelatin in PBS was added. After a 1 hour incubation, plates were washed with PBS containing 0.05% Tween-20, and enzyme substrate, 3.8 mM paranitrophenylphosphate in 1M diethanolamine with 1 mM $MgCl_2$, pH 9.8 was added. The presence of antibody to 16OHE1-glucuronide fraction was seen by the development of a yellow color read at 405 nm in a microtiter plate reader. The isotypes of monoclonal antibodies were determined similarly, except that rabbit anti-mouse IgG heavychain- and/or light chain-specific antibody:alkaline phosphatase conjugates were used (Zymed, San Francisco, Calif. U.S.A.).

Mab 4C11 to 2OHE1-Glucuronide Fraction

All monoclonal antibodies were made by fusing splenocytes from female Balb/C mice immunized with 2-Hydroxyestrone (2OHE1)-KLH estrogen:protein conjugates with non-immunoglobulin secreting murine myeloma cell line SP2/O-AG14 (ATCC CRL1581). It is preferred that 2OHE1 derivatives for conjugation to enzymes and other proteins be synthesized as described by Ball et al. in Steroids 31:249–258, 1978 and be linked to protein following Mattox, Litwiller, and Nelson in J Steroid Biochem 10:167–172, 1979. Following these methods, the 2OHE1 derivatives are made as the 17-carboxymethyloxime and linked to proteins through the C-17 position of 2OHE1. A preferred method for preparing 2OHE1-3-glucuronide and 2OHE1-3-glucuronide-labeled enzymes and proteins for use according to this invention is isolation from late pregnancy urine and conjugation to enzymes and proteins as described by Samarajeewa, Leepipatpaiboon, and Coulson in Steroids 36:611–618, 1980.

Six 10–14 week old female Balb/C mice were immunized i.p. with 50–100 ug of 2OHEE1-KLH conjugate in 0.5 mL of TiterMax adjuvant (CytRx Corporation, Norcross Ga. U.S.A.) in PBS (50:50 v/v). Animals were boosted i.p. with 50–100 ug of emulsified antigen in TiterMax at monthly intervals for three months, or until mice demonstrated antibody to conjugate. Mice were bled and tested for antibody to 2OHE1 every two weeks in an ELISA similar to that used for antibodies to 2MeoE1 (described below). Mice with highest titers were injected intravenously with 100 ug of 2OHE1-KLH in sterile saline via the tail vein 4 days prior to cell fusion. Spleen cells at 5:1 ratio with SP2/O cells were fused with 30% polyethylene glycol 1000, and distributed in 0.2 mL aliquots into ten 96-well culture plates at $2 \times 10^4$ cell per well in media containing Hybridoma Enhancing Medium (HEM, Sigma Chemical Company, St. Louis, Mo. U.S.A.). The growth media consisted of RPMI 1640, 10% heat-inactivated fetal bovine serum, 0.1 mM MEM nonessential amino acids, 2mM glutamine, and HAT (hypothanxine/aminopterin/thymidine; 100:0.4: $16 \times 10^{-6}$M). After a majority of the hybridomas had grown to confluence (about 10–14 days), all 960 wells were screened simultaneously for antibodies to 2OHE1.

The presence of antibodies to 2OHE1 and/or 2OHE1-glucuronide fraction was determined by a specific ELISA as described above for antibodies to 16OHE1 using 2OHE1-17-linked alkaline phosphatase. The isotypes of monoclonal antibodies were determined similarly, except that rabbit anti-mouse IgG heavy chain and/or light chain-specific antibody:alkaline phosphatase conjugates were used (Zymed, San Francisco, Calif. U.S.A.).

MAb 9D3 to 2MeoE1-Glucuronide Fraction

All monoclonal antibodies were made by fusing splenocytes from female Balb/C mice immunized with 2-Methoxyestrone (2MeoE1)-KLH estrogen:protein conjugates with non-inmunoglobulin secreting murine myeloma cell line SP2/O-AG14 (ATCC CRL1581). It is preferred that 2MeoE1 derivatives for conjugation to enzymes and other proteins be synthesized as described by Ball et al. in Steroids 31:249–258, 1978 and be linked to protein following Mattox, Litwiller, and Nelson in J Steroid Biochem 10:167–172, 1979. Following these methods, the 2MeoE1 derivatives are made as the 17-carboxymethyloxime and linked to proteins through the C-17 position of 2MeoE1. A preferred method for preparing 2MeoE1-3-glucuronide and 2MeoE1-3-glucuronide-labeled enzymes and proteins for use according to this invention is isolation from late pregnancy urine and conjugation to enzymes and proteins as described by Samarajeewa, Leepipatpaiboon, and Coulson in Steroids 36:611–618, 1980.

Six 10–14 week old female Balb/C mice were immunized i.p. with 50–100 ug of 2MeoE1-KLH conjugate in 0.5 mL of TiterMax adjuvant (CytRx Corporation, Norcross Ga. U.S.A.) in PBS (50:50 v/v). Animals were boosted i.p. with 50–100 ug of emulsified antigen in TiterMax at monthly intervals for three months, or until mice demonstrated antibody to conjugate. Mice were bled and tested for antibody to 2MeoE1 every two weeks in an ELISA similar to that used for antibodies to 2MeoE1 (described above). Mice with highest titers were injected intravenously with 100 ug of 2MeoE1-KLH in sterile saline via the tail vein 4 days prior to cell fusion. Spleen cells at 5:1 ratio with SP2/O cells were fused with 30% polyethylene glycol 1000, and distributed in 0.2 mL aliquots into ten 96-well culture plates at $2\times10^4$ cell per well in media containing Hybridoma Enhancing Medium (HEM, Sigma Chemical Company, St. Louis, Mo. U.S.A.). The growth media consisted of RPMI 1640, 10% heat-inactivated fetal bovine serum, 0.1 mM MEM nonessential amino acids, 2 mM glutamine, and HAT (hypothanxine/aminopterin/thymidine; 100:0.4: $16\times10^{-6}$M). After a majority of the hybridomas had grown to confluence (about 10–14 days), all 960 wells were screened simultaneously for antibodies to 2MeoE1.

The presence of antibodies to 2 MeoE1 and/or 2MeoE1-glucuronide fraction was determined by a specific ELISA as described above for antibodies to 16OHE1 using 2MeoE1-17-linked alkaline phosphatase. The isotypes of monoclonal antibodies were determined similarly, except that rabbit anti-mouse IgG heavy chain and/or light chain-specific antibody:alkaline phosphatase conjugates were used (Zymed, San Francisco, Calif. U.S.A.).

Characterization of Monoclonal Antibodies

All cell lines which bound 16OHE1-alkaline phosphatase underwent at least two subclonings by limiting dilution to insure monoclonality prior to characterization.

Specificities of antibodies to 16OHE1 metabolites were determine by a competitive inhibition ELISA, but with decreasing concentrations of (10 to 0 ug/mL) of the estrogen, androgen, or non-steroidal compound to be tested for cross-reactivity. The specificity of each monoclonal antibody for its antigen was defined as per cent cross-reactivity, and reflects the relative affinities of the antibody for different antigens. Cross-reactivity was defined as the ratio of concentrations of tested compounds to concentration of 16OHE1 required to give 50% inhibition of 16OHE1-labeled enzyme binding in the competitive ELISA, times 100. Monoclonal antibodies to 16OHE1 were tested for specificity against 16OHE1 conjugates and against structurally related estrogen and androgen metabolites, particularly against 16α-hydroxylated steroids. Monoclonal antibodies for use in the present invention were selected to react nearly equivalently with 16OHE1 and 3-substituted 16OHE1, that is to react with said 16OHE1-glucuronide fraction. Not all monoclonal antibodies to 16OHE1 generated as described above demonstrated specific reactivity with the said 16OHE1-glucuronide fraction.

The relative affinities of monoclonal antibodies to 16OHE1 metabolites were determined by doing the competitive inhibition ELISA with decreasing amounts of 16OHE1(1000 to 0 pg/mL) in the presence of a fixed amount of 16OHE1-alkaline phosphatase and monoclonal antibody in the wells of a microtiter plate (see Competitive Direct Enzyme-linked Immunoassay, above). Affinities were estimated assuming that the concentration of estrogen at 50% inhibition in the ELISA equals the reciprocal of the association constant, $K_a$.

The specificity and affinity of four monoclonal antibodies for use in the assays of the present invention are given in Table 1. All antibodies demonstrated similar apparent reactivities with 16OHE1 and 16OHE1-3-glucuronide (100±15%), and of the twelve metabolites tested, significant cross-reactivity of about 3% was seen for only 5-androsten-3β,16α-diol-17-one and 5α-androstan-3β,16β-diol-17-one. These 16α-of-17-one androgens cross-react because their flat A/B- rings and equatorial 3-hydroxyl groups allows them to partially "fit" the anti-16OHE1 antibody binding site. These metabolites are only found at measurable concentrations during the last trimester of pregnancy. The affinities ($K_a$) of the monoclonal antibodies varied from 0.5 to $5\times10^{11}$ L/Mole. The isotype of all antibodies to said 16OHE1-glucuronide fraction is $IgG_1$ with lambda light chain.

All cell lines which bound 2OHE1-alkaline phosphatase underwent at least two subclonings by limiting dilution to insure monoclonality prior to characterization. Specificities of antibodies to 2OHE1 metabolites were determined by a competitive inhibition ELISA, but with decreasing concentrations of (10 to 0 ug/mL) of the estrogen, to be tested for cross-reactivity, as described above for monoclonal antibodies to 16OHE1. Monoclonal antibodies to 2OHE1 were tested for specificity against 2OHE1 conjugates and against structurally related estrogens, particularly against 2-methoxylated steroids. Monoclonal antibodies for use in the present invention were selected to react nearly equivalently with 2OHE1 and 3-substituted 2OHE1, that is to react with said 2OHE1-glucuronide fraction. Not all monoclonal antibodies to 2OHE1 generated as described above demonstrated specific reactivity with the said 2OHE1-glucuronide fraction.

The relative affinities of monoclonal antibodies to 2OHE1 metabolites were determined by doing the competitive inhibition ELISA with decreasing amounts of 2OHE1 (1000 to 0 pg/mL) in the presence of a fixed amount of 2OHE1-alkaline phosphatase and monoclonal antibody in the wells of a microtiter plate (see Competitive Direct Enzyme-linked Immunoassay, above).

The specificity and affinity of one monoclonal antibody to 2OHE1-glucuronide fraction for use according to the present invention is given in Table 2. The antibody demonstrates similar apparent reactivities with 2OHE1 and 2OHE1-3-glucuronide (80%), and of the 10 metabolites tested, significant cross-reactivity was seen for all other 2-hydroxylated estrogens, 2-hydroxyestradiol and 2-hydroxyestriol. The affinity ($K_a$) of the monoclonal antibody is about $1\times10^{11}$ L/Mole. The isotype of all antibodies to said 2OHE1-glucuronide fraction is $IgG_1$ with kappa light chains.

The specificity and affinity of one monoclonal antibody to 2MeoE1-glucuronide fraction, 9D3, for use according to the present invention is given in Table 3. The antibody demonstrates similar apparent reactivities with 2MeoE1 and 2MeoE1-3-glucuronide (120%), and of the 10 metabolites tested, significant cross-reactivity was seen for all other 2-methoxylated 2-hydroxyestrogens; 2-methoxy 2-hydroxyestradiol and 2-methoxy 2-hydroxyestriol. The affinity ($K_a$) of the monoclonal antibody is about $2\times10^{11}$ L/Mole. The isotype of all antibodies to said 2MeoE1-glucuronide fraction is $IgG_{1,2b}$ (mixed type) with lambda light chains.

TABLE 1

Specificity and Affinity of Monoclonal Antibodies to 16α-Hydroxyestrone

| | % CROSS-REACTIVITY Monoclonal Antibody Designation | | | |
|---|---|---|---|---|
| Steroid Metabolite | 12C2 | 16F11 | 19H7 | 12D7 |
| 1,3,5[10]-Estratrien-3,16α-diol-17-one (16OHE1) | 100.0 | 100.0 | 100.0 | 100.0 |
| 1,3,5[10]Estratrien-3,16α-diol-17-one-3-glucuronide | 90.0 | 90.0 | 90.0 | 90.0 |
| 5-Androsten-3β,16α-diol-17-one | 3.6 | 3.0 | 3.6 | 3.3 |
| 5α-Androstan-3β,16α-diol-17-one | 3.0 | 3.2 | 3.1 | 3.1 |

TABLE 1-continued

Specificity and Affinity of Monoclonal Antibodies to 16α-Hydroxyestrone

| | % CROSS-REACTIVITY Monoclonal Antibody Designation | | | |
|---|---|---|---|---|
| Steroid Metabolite | 12C2 | 16F11 | 19H7 | 12D7 |
| 4-Androsten-16α-ol-3,17-dione | 0.8 | 0.5 | 0.2 | 0.5 |
| 5α-Androstan-3α,16α-diol-17-one | 0.8 | 0.5 | 0.2 | 0.5 |
| 5β-Androstan-3α,16α-diol-17-one | 0.0 | 0.0 | 0.0 | 0.0 |
| 5β-Androstan-3β,16α-diol-17-one | 0.0 | 0.0 | 0.0 | 0.0 |
| 1,3,5[10]-Estratrien-3,16α,17α-triol | 0.7 | 0.6 | 0.5 | 0.9 |
| 1,3,5[10]-Estratrien-3,17β-diol-16-one | 0.2 | 0.2 | 0.2 | 0.2 |
| 1,3,5[10]-Estratrien-3.16α,17β-triol | <0.1 | <0.1 | <0.1 | <0.1 |
| 1,3,5[10]-Estratrien-3,17β-diol | <0.1 | <0.1 | <0.1 | <0.1 |
| 1,3,5[10]-Estratrien-3-ol-17-one | <0.1 | <0.1 | <0.1 | <0.1 |
| ISOTYPE (all IgG1, lambda light chain) | IgG1 | IgG1 | IgG1 | IgG1 |
| AFFINITY ($K_a$, L/mole × $10^{11}$) | 5.0 | 3.0 | 2.0 | 0.5 |

TABLE 2

Specificity and Affinity of Monoclonal Antibody to 2-Hydroxyestrone

| Steroid Metabolite | % CROSS-REACTIVITY Monoclonal Antibody Designation |
|---|---|
| | 4C11 |
| 1,3,5[10]-Estratrien-3-ol-17-one (2OHE1) | 100.0 |
| 1,3,5[10]-Estratrien-3-ol-17-one-3-glucuronide (2OHE1-3-glucuronide) | 80.0 |
| 1,3,5[10]-Estratrien-3,17β-diol-2 (2OHE2) | 100.0 |
| 1,3,5[10]-Estratrien-2,3,16,17β-tetrol (2OHE3) | 70.0 |
| 1,3,5[10]-Estratrien-3,4-diol-17-one | 2.1 |
| 1,3,5[10]-Estratrien-3,16α,17β-triol | 0.2 |
| 1,3,5[10]-Estratrien-3,17β-diol-16-one | 0.0 |
| 1,3,5[10]-Estratrien-3-ol-17-one | 0.2 |
| 1,3,5[10]-Estratrien-3,17β-diol | 0.0 |
| 1,3,5[10]-Estratien-2,3-diol-17-one 2-methyl ether | 0.0 |
| ISOTYPE (IgG1, kappa light chain) | IgG1 |
| AFFINITY ($K_a$, L/mole × $10^{11}$) | 1.0 |

TABLE 3

Specificity and Affinity of Monoclonal Antibody to 2-Methoxyestrone

| Steroid Metabolite | % CROSS-REACTIVITY Monoclonal Antibody Designation |
|---|---|
| | 9D3 |
| 1,3,5[10]-Estratrien-3-ol-17-one-2-methoxy (2MeoE1) | 100.0 |
| 1,3,5[10]-Estratrien-3-ol-17-one-2-methoxy-3-glucuronide (2MeoE1-3-glucuronide) | 120.0 |
| 1,3,5[10]-Estratrien-3,17β-diol-2-methoxy (2MeoE2) | 100.0 |
| 1,3,5[10]-Estratrien-3,16,17β-triol-2-methoxy (2MeoE3) | 70.0 |
| 1,3,5[10]-Estratrien-17-one-2,3-dimethoxy | <0.1 |
| 1,3,5[10]-Estratrien-3,17β-diol-16-one | 0.0 |
| 1,3,5[10]-Estratrien-3,16α,17β-triol | 0.0 |
| 1,3,5[10]-Estratrien-3,17β-diol | 0.0 |
| 1,3,5[10]-Estratrien-3-ol-17-one | 0.0 |
| ISOTYPE (IgG1 ,2b; lambda light chain) | 1,2b |
| AFFINITY ($K_a$, L/mole × $10^{11}$) | 2.0 |

Direct ELISA for said 16OHE1-glucuronide Fraction in Serum

Polystyrene microtiter plates (96 well, C96 Maxisorb plate, NUNC, Napierville, Ill. U.S.A.) were coated with 200 ng/well affinity purified rabbit anti-mouse IgG, Fc-fragment specific antibody (Jackson Immunoresearch, West Grove Pa. U.S.A.) in PBS and incubated overnight at room temperature. The plates were washed with PBS, blocked with 0.5% casein (w/v) in PBS, and stored wet until use. Assay Standards were prepared by serial dilution of 16OHE1-3-glucuronide in steroid-free (charcoal-extracted) human serum at concentrations ranging from 7.8 to 1000 pg/mL. Preparation of charcoal-extracted serum is a well established procedure in the diagnostic arts.

For assay, twenty-five uL of serum, Standards, and Positive and Negative Controls were aliquoted in duplicate into an 8×12 array of racked 1.2 mL microtubes (CalCon Incorporated, Claremont, Calif. U.S.A.). Microtubes are arranged in a pattern congruous with that of the ELISA plate assay wells such that liquid may be transferred directly from tubes to the assay well with an eight-channel pipettor. Sample aliquots were diluted 1:7 (v/v) by addition of 150 uL of 0.05M 2-[Morpholino]ethanesulfonic acid (MES) buffered saline (MESBS), pH 6.5, 2 mM EGTA, 5 mM ascorbic acid, 50 ng/mL dehydrotestosterone (DHT) containing 3 ng/mL of purified monoclonal antibody (Sample Diluent). Diluted sera samples were covered and incubated at 38 deg C. in a water bath for one hour. After cooling for 15 minutes, 75 uL of standards, controls, and unknowns were transferred to wells of a washed rabbit anti-mouse IgG Fc antibody-coated microtiter ELISA plate with an eight-channel pipettor. To these wells was then added and additional 75 uL of a 1:2000 dilution (v/v) of 16OHE1-labeled AP (3000 U/mL) in Tris-buffered saline, pH 6.9, (TBS) containing 0.1% gelatin, pH 6.5 (Conjugate Diluent), and plates were covered and incubated overnight at 4 deg C. Plates were washed six times with TBS containing 0.05% Tween-20, and 150 uL of AP Enzyme Substrate containing 2 mM paranitrophenol phosphate (pNPP) in 1M diethanolamine was added to quantify 16OHE1-labeled AP bound to the plate. Absorbance at 450 nm was read with an automated ELISA plate reader after 30 minutes. The concentration of said 16OHE1-glucuronide fraction in unknowns was determined by reference and extrapolation from the standard curve using a four-parameter logistic curve fitting program (Kineti-Calc, Biotek Instruments, Wynooski, Vt. U.S.A.).

Direct ELISA for Total 16OHE1-Glucuronides in Serum

The assay for total 16OHE1-glucuronides in serum is done exactly as described above, except that all 16OHE1- glucuronides, both 3- and 16-glucuronides are deconjugated, that is, the glucuronides removed from estrogens in serum, prior to performing the ELISA. Standards for this assay are prepared by serial dilution of 16OHE1 in charcoal-extracted serum at 7.8 to 1000 pg/mL. Cleavage of steroidal glucuronides is achieved by incubation with the enzyme β-glucuronidase, preferably that isolated from the bacteria, E. Coli. In practice, E. Coli β-glucuronidase (Sigma Chemical Company, St. Louis Mo. U.S.A.), 1000 U/mL, is added to the MESBS serum dilution buffer, and the assay performed exactly as described above for Direct ELISA for 16OHE1-3-glucuronide Fraction. By this modification of the preferred assay of this invention, concentrations detected and /or quantified by direct ELISA with antibodies of this invention will be equal to or greater than those found by direct ELISA for said 16OHE1-glucuronide fraction (no deconjugation).

Each of the two direct ELISA formats described above, when utilized with monoclonal antibodies described above, will find greatest use in various situations. For example, the direct ELISA for said 16OHE1-glucuronide fraction is preferable when used for the diagnosis/prognosis of neoplastic diseases. Different pathological states, as, for example, neoplastic versus autoimmune disease, may be associated with distinctive patterns of 16OHE1 conjugation. Different enzyme pretreatment of 16OHE1 metabolites in body fluids, therefore, may be required to optimally distinguish and detect specific pathological conditions.

APAAP Immunocytochemical Assay for 16OHE1-glucuronide Fraction in Tissue Sections Sections of 5 to 10 micron thickness cut from paraformaldehyde-fixed, paraffin-embedded tissues with a microtome are mounted on dry glass slides previously treated with 5% swine serum in PBS. Slides are heated at 60 degrees C. for 30 minutes and dewaxed immersion in xylene for 5 min. Tissues sections on slides are rehydrated by repetitive immersion in a graded series of ethanol/water solutions: 100% ethanol (3 min.); 95% ethanol (3 min.); 70% ethanol (3 min); and, finally, PBS (2×3 min.). Rehydrated tissues are immediately overlaid and incubated with 100 uL of monoclonal antibody at 5 ug/mL in TBS (Anti-16OHE1 Antibody Solution) for 30 min at room temperature. Slides are then washed by immersion in TBS (6×3 min) to remove antibody not bound to said 16OHE1-glucuronide fraction in tissue sections. One hundred uL of a solution containing polyclonal rabbit anti-mouse IgG Antibody Bridging Solution (DAKO Corporation, Carpenteria Calif. U.S.A.) in PBS is overlaid onto each tissue section, and incubated for 1 hr at room temperature. Slides with tissues are washed as in the previous step and tissues overlaid with a 100 uL aliquot of alkaline phosphatase:anti-alkaline phosphatase (APAAP Complex) (DAKO) in TBS for 30 min . The optimal dilution of anti-mouse IgG antisera (Antibody Bridging Solution) and APAAP Complex should be determined by titration, but should be about 1:25 in TBS, pH 7.4. After washing, tissues are incubated with 100 uL of napthol AS-MX/Fast Red Enzyme Substrate for 10 min. The enzyme substrate is prepared as follows. Dissolve 2 mg napthol AS-MX phosphate (Sigma Chemical Company, St. Louis Mo. U.S.A.) in 0.2 mL of N,N-dimethyl formamide in a glass tube, and add 10 mL of 0.1M TBS, pH 8.2 (Enzyme Substrate Solution). Immediately before use, dissolve Fast Red TR salt (Sigma) at 12 mg/mL in the napthol AS-MX solution and apply to the washed slides. Endogenous alkaline phosphatase activity in the mammalian tissues may be inhibited by adding 1 mM levamisole (Sigma) to the later solution. After an intense red color develops, substrate is washed from the slide with water, and after blotting excess liquid, the tissues are preserved on the slides by mounting with glycerol vinyl alcohol solution (GVA Mount, Zymed, San Francisco Calif. U.S.A.) and coverslipped for permanent storage.

Direct ELISA for said 2OHE1-glucuronide Fraction in Serum

The assay is done in a manner very similar to that for 16OHE1-glucuronide fraction (above). Polystyrene microtiter plates were coated with affinity purified rabbit anti-mouse IgG, Fc-fragment specific antibody in PBS and incubated overnight at room temperature. The plates were washed with PBS, blocked with 0.5% casein (w/v) in PBS, and stored wet until use. Assay Standards were prepared by serial dilution of 2OHE1-3-glucuronide in steroid-free (charcoal-extracted) human serum at concentrations ranging from 7.8 to 1000 pg/mL.

For assay, twenty-five uL of serum, Standards, and Positive and Negative Controls were aliquoted in duplicate into an 8×12 array of racked 1.2 ml microtubes. Sample aliquots were diluted 1:7 (v/v) by addition of 150 uL of 0.05M 2-[Morpholino]ethanesulfonic acid (MES) buffered saline (MESBS), pH 6.5, with EGTA and ascorbate (as above) containing 3 ng/mL of purified monoclonal antibody (Sample Diluent). Diluted sera samples were covered and incubated at 38 deg C. in a water bath for one hour. After cooling for 15 minutes, 75 uL of standards, controls, and unknowns were transferred to wells of a washed rabbit anti-mouse IgG Fc antibody-coated microtiter ELISA plate. To these wells was then added and additional 75 uL of a 1:2000 dilution (v/v) of 2OHE1-labeled AP (3000 U/mL) in TBS containing 0.1% gelatin, pH 6.9 (Conjugate Diluent), and plates were covered and incubated overnight at 4 deg C. Plates were washed six times with TBS containing 0.05% Tween-20, and 150 uL of AP Enzyme Substrate pNPP was added to quantity 2OHE1-labeled AP bound to the plate. Absorbance at 450 nm was read after 30 minutes with an automated ELISA plate reader. The concentration of said 2OHE1-glucuronide fraction in unknowns was determined by reference and extrapolation from the standard curve.

Direct ELISA for Total 2OHE1, 2OHE2, and 2OHE3-Glucuronides in Serum

The assay for total 2-hydroxylated estrogen glucuronides in serum is done exactly as described for 2OHE1-glucuronides above, except that all 2-hydroxylated-glucuronides, including 2OHE2- and 2OHE3-glucuronides are deconjugated, that is, the glucuronides removed from estrogens in serum, prior to performing the ELISA. This is possible because Mab 4C11 recognizes all unconjugated 2-hydroxylated estrogens, not just the 2OHE1. Standards for this assay are prepared by serial dilution of 2OHE1 in charcoal-extracted serum at 7.8 to 1000 pg/mL. Cleavage of steroidal glucuronides in serum is achieved by incubation with the enzyme β-glucuronidase, preferably that isolated from the bacteria, E. Coli. In practice, E. Coli β-glucuronidase, 1000 U/mL, is added to the MESBS serum dilution buffer, and the assay performed exactly as described above for Direct ELISA for 2OHE1-3-glucuronide Fraction. By this modification of the preferred assay of this invention, concentrations detected and/or quantified by direct ELISA with antibodies of this invention will be generally equal to or greater than those found by direct ELISA for said 2OHE1-glucuronide fraction (no deconjugation).

Each of the two direct ELISA formats described above, when utilized with monoclonal antibodies described above, will find greatest use in various situations. For example, the direct ELISA for said 2OHE1-glucuronide fraction is preferable when used for the diagnosis/prognosis of neoplastic diseases. Different pathological states, as, for example, neoplastic versus autoimmune disease, may be associated with distinctive patterns of 16OHE1 conjugation. Different enzyme pretreatment of 16OHE1 metabolites in body fluids, therefore, may be required to optimally distinguish the glucuronide fraction and detect specific pathological conditions.

APAAP Immunocytochemical Assay for 2OHE1-glucuronide Fraction in Tissue Sections This method follows that for immunocytochemical detection for 16OHE1-glucuronide, above. Sections of 5 to 10 micron thickness cut from paraformaldehyde-fixed, paraffin-embedded tissues with a microtome are mounted on dry glass slides previously treated with 5% swine serum in PBS. Slides are heated at 60 degrees C. for 30 minutes and dewaxed immersion in xylene for 5 min. Tissues sections on slides are rehydrated by repetitive immersion in a graded series of ethanol/water solutions: 100% ethanol (3 min.): 95% ethanol (3 min.); 70% ethanol (3 min); and, finally, PBS (2×3 min.). Rehydrated tissues are immediately overlaid and incubated with 100 uL of monoclonal antibody at 20 ug/mL in TBS (Anti-2OHE1 Antibody Solution) for 30 min at room temperature. Slides are then washed by immersion in TBS (6×3 min) to remove antibody not bound to said 2OHE1-glucuronide fraction in tissue sections. One hundred uL of a solution containing polyclonal rabbit anti-mouse IgG Antibody Bridging Solution in PBS is overlaid onto each tissue section, and incubated for 1 hr at room temperature. Slides with tissues are washed as in the previous step and tissues overlaid with a 100 uL aliquot of alkaline phosphatase:anti-alkaline phosphatase (APAAP Complex) in TBS for 30 min. After washing, tissues are incubated with 100 uL of napthol AS-MX/Fast Red Enzyme Substrate for 10 min. The enzyme substrate is prepared as follows. Dissolve 2 mg napthol AS-MX phosphate (Sigma Chemical Company, St. Louis Mo. U.S.A.) in 0.2 mL of N,N-dimethyl formamide in a glass tube, and add 10 mL of 0.1M TBS, pH 8.2 (Enzyme Substrate Solution). Immediately before use, dissolve Fast Red TR salt (Sigma) at 12 mg/mL in the napthol AS-MX solution and apply to the washed slides. Endogenous alkaline phosphatase activity in the mammalian tissues may be inhibited by adding 1 mM levamisole (Sigma) to the later solution. After an intense red color develops, substrate is washed from the slide with water, and after blotting excess liquid, the tissues are preserved on the slides by mounting with glycerol vinyl alcohol solution and coverslipped for permanent storage.

Direct ELISAs for 2MeoE1-Glucuronide Fraction in Serum

The assay for 2MeoE1-glucuronide fraction in serum is done exactly as described above for 16OHE1-glucuronide fraction, except that antibody to 2MeoE1 (9D3), 3 ng/mL, is used with 2MeoE1-labeled-AP (1:2000). Standards for this assay are prepared by serial dilution of 2MeoE1-3-glucuronide in charcoal-extracted serum at 7.8 to 1000 pg/mL.

Direct ELISA for Total 2-Methoxylated 2OHE1-, 2OHE2-, and 2OHE3-Glucuronide Fractions in Serum The assay for total 2-methoxylated 2-hydroxyestrogen glucuronides in serum is done exactly as described for 2MeoE1-glucuronides above, except that all 2-methoxylated-glucuronides, including 2MeoE1-, 2MeoE2- and 2MeoE3-glucuronides are deconjugated, that is, the glucuronides removed from estrogens in serum, prior to performing the ELISA. This is possible because Mab 9D3 recognizes all unconjugated 2-methoxylated estrogens, not just the 2MeoE1. Standards for this assay are prepared by serial dilution of 2MeoE1 in charcoalextracted serum at 7.8 to 1000 pg/mL. Cleavage of steroidal glucuronides in serum is achieved by incubation with the enzyme $\mu$-glucuronidase, preferably that isolated from the bacteria, *E. Coli*. In practice, *E. Coli* β-glucuronidase, 1000 U/mL, is added to the MESBS serum dilution buffer, and the assay performed exactly as described above for direct ELISA for 2MeoE1-3-glucuronide Fraction. By this modification of the preferred assay of this invention, concentrations detected and/or quantified by direct ELISA with antibodies of this invention will be equal to or greater than those found by direct ELISA for said 2MeoE1-glucuronide fraction (no deconjugation). This assay format, in fact, measures the sum of 2MeoE1, 2MeoE2 (2-methoxyestradiol), and 2MeoE3 (2-Methoxyestriol) glucuronide fractions, and is, therefore, also an assay for this fraction in serum.

Each of the two direct ELISA formats described above, when utilized with monoclonal antibodies described above, will find greatest use in various situations, some described in the following examples.

EXAMPLE 1

Normal and Breast Cancer Sera in Direct ELISA for 16OHE1-Glucuronide Fraction

Figure 5:
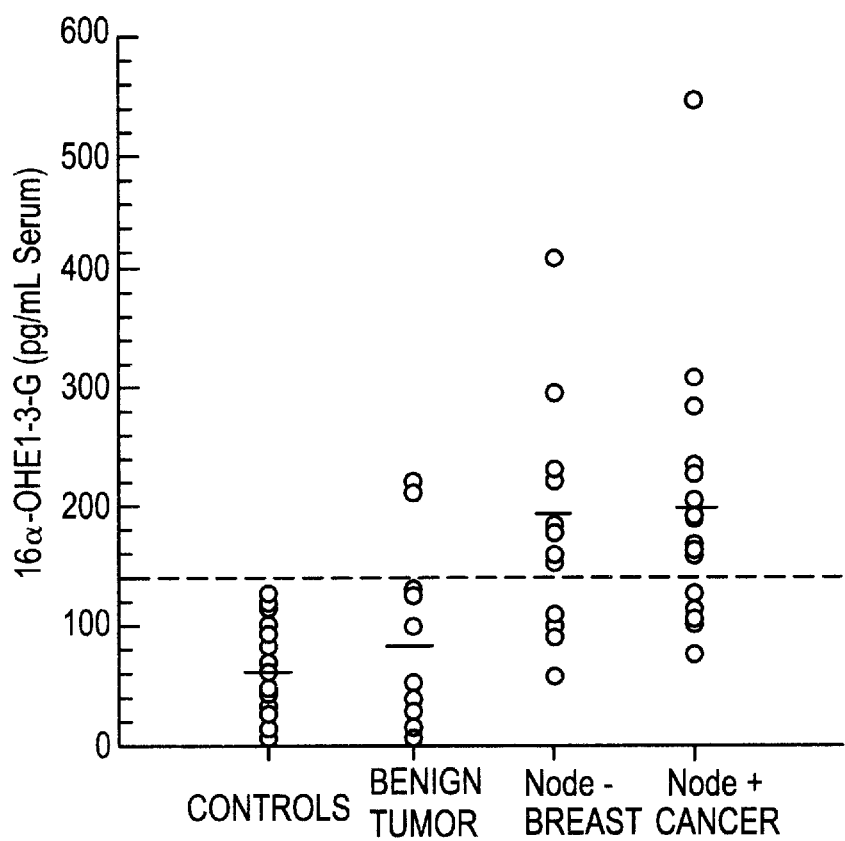
FIG. 5 is a graph comparing the levels of the 16OHE1-glucuronide fraction in sera of healthy women to those of women with benign breast disease and both node-negative and node-positive breast cancer.

Seventeen sera from healthy women not taking estrogens or other drugs (from Jewish Hospital, St. Louis Mo. U.S.A.), and 28 sera from women with pathologically confirmed and staged breast cancer tumors at the time when serum was collected (from Case Western Reserve, Cleveland, Ohio, U.S.A., and Ohio State University, Columbus, Ohio, U.S.A.) were assayed by the direct competitive assay for the 16OHE1-glucuronide fraction, herein after called "serum 16OHE1" as described above, and the results shown graphically in FIG. 5. Serum from these patients was collected on the day of surgery to remove the tumors by mastectomy. Most of the surgeries were performed subsequent to earlier biopsies or lumpectomies that removed portions of the breast tumors.

Only those women who were found to have residual malignant tissues are included in this study.

The average of serum 16OHE1 for 28 women with breast cancer tumors was about 200 pg/mL (TABLE 4). The presence or absence of tumor cell metastases to the lymphatic nodes system was known in these patients, that is, whether they were node positive or node negative, respectively. The 11 patients with positive nodes and 17 node negative patients both had about 200 pg/mL serum 16OHE1. The levels of serum 16OHE1 in 11 healthy postmenopausal women was about 60 pg.mL, with none of the women having serum 16OHE1-glucuronide fraction above 140 pg/mL. Nine of 11 (81%) node positive women had serum 16OHE1-glucuronide fraction greater than 140 pg/mL, and the same fraction of node negative women had serum values in excess of 140 pg/mL. This data indicates that serum 16OHE1-glucuronide fraction is a marker for the potential presence of a breast cancer tumor. Odds Ratio analysis indicates that a woman with serum 16OHE1>140 pg/mL would have at least an eight-fold higher risk of developing breast cancer. It also follows that the higher the level of serum 16OHE1 in a woman, the greater is the likelihood of the disease and/or occult tumor mass.

These results further illustrate the utility of the level of serum 16OHE1 (the glucuronide fraction) as a tumor marker, and 16OHE1-glucuronide fraction as a tumor-associated antigen.

TABLE 4

Patients' ages and serum 16αOHE1 concentration

|  | CONTROLS | CONTROLS | BENIGN | BREAST CANCER | |
|---|---|---|---|---|---|
|  | (Premeno.) | (Premeno.) | TUMOR | Node − | Node + |
| DETAILS | (N = 12) | (N = 16) | (N = 12) | (N = 11) | (N = 16) |
| AGE (Yr) | 32 (11.6)* | 65.2(7.8) | 62.5(6.9) | 69.8(8.4) | 68.8(7.9) |
| 16αOHE1 | 184(50.2) | 60.8(39.1) | 83.8(81.1) | 192.0(106.0)** | 202.1(112.9)*** |

*Mean (SD).
**$p<0.0003$ and $p<0.01$ for Node − versus Controls and Benign Tumor, respectively by one sided Mann-Whitney U-test.
***$p<0.0001$ and $p<0.003$ for Node + versus Control and Benign Tumor, respectively.

EXAMPLE 2

Normal and Breast Cancer Sera in Direct ELISA for Total Serum 16OHE1-Glucuronide The same sera as used in Example 1, above, were assayed for total serum 16OHE1-glucuronide by the ELISA described above. This assay differed from that used in Example 1 in that prior deconjugation with β-glucuronidase allows detection and/or quantification of 16OHE1-3,16-glucuronides in addition to the said 16OHE1-glucuronide fraction.

Figure 6:
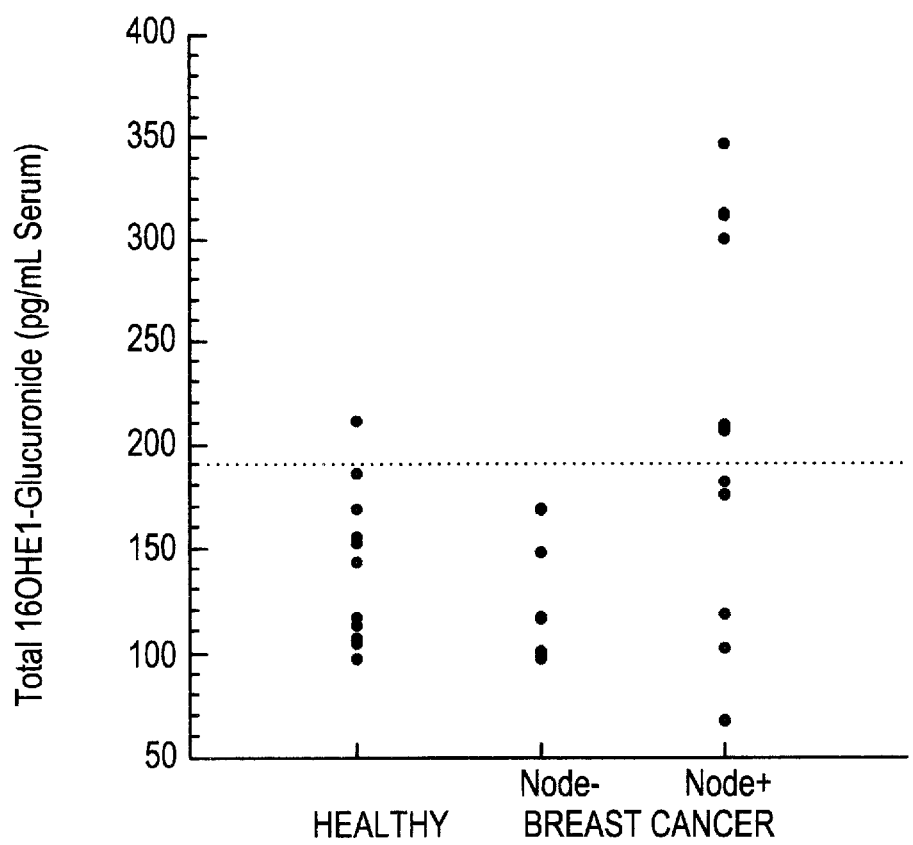
FIG. 6 is a graph comparing the levels of the total 16OHE1 in sera of healthy women to those of women with both node-negative and node-positive breast cancer.

The average total serum 16OHE1 glucuronide for 11 healthy postmenopausal women was 142±35 pg/mL, as compared to 201±93 pg/mL for the node positive breast cancer patients, and 133±33 pg/mL for the node negative patients (see FIG. 6). There is less discrimination between normals and node positive breast cancer patients groups for total serum 16OHE1-glucuronide than for serum 16OHE1-glucuronide fraction. This appears to be due to a greater amount of serum 16OHE1-3,16-glucuronides, as shown graphically in FIG. 2, as compared to the amount of 16OHE1-glucuronide fraction in healthy women, as shown graphically in FIG. 2. The direct ELISA of 16OHE1-glucuronide fraction is, therefore, preferred for detection of elevations in serum 16OHE1 metabolites in breast cancer. The ELISA for total 16OHE1-glucuronides, however, may prove useful in certain circumstances, as in other body fluids such as breast aspirates, or other types of malignancies, or diseases.

EXAMPLE 3

Fixed Normal and Breast Cancer Tissue in APAAP Direct Immunocytochemical Assay for 16OHE1-Glucuronide Fraction Formalin-fixed paraffin-embedded breast tissue blocks from 12 healthy women undergoing breast reduction surgery, and blocks of breast tumor tissue and matched Near Adjacent Tissue (NAT) from 8 women with breast cancer were obtained from Ohio State University, Columbus, Ohio U.S.A. The NAT is collected from tissues that immediately surround the solid breast tumors, and is used to define the margins and extent of tumor. Tissue blocks were sectioned, dewaxed and stained for 16OHE1-glucuronide fraction as described above in APAAP Immunocytochemical Assay for said 16OHE1-glucuronide Fraction in Tissue Sections. Both tumor and matched NAT were stained for each tumor. Each tissue section was stained with four reagents: 1) monoclonal antibody to 16OHE1-glucuronide fraction; 2) monoclonal antibody to 16OHE1-glucuronide fraction with excess 16OHE1 added; 3) monoclonal antibody to 16OHE1-glucuronide fraction with excess estradiol added; and 4) nonimmune polyclonal mouse IgG at same concentration as specific monoclonal antibody. These last three stains acted as controls for specific and nonspecific staining. Thus, a pattern of specific staining would see: 1) positive; 2) negative; 3) positive: and 4) negative. The intensity of staining is ranked subjectively as negative (−), weakly positive (±), positive (+), and strongly positive (++).

Examples of breast tissues stained for 16OHE1 are illustrated in FIGS. 7A and 7B wherein a breast cancer near adjacent tissue (NAT) and tissue from a normal breast are stained for 16OHE1-glucuronide fraction according to the APAAP direct immunocytochemical assay method of this invention. The breast tumor (NAT) tissue (Patient 7893) demonstrates bright red staining surrounding the ductal elements, whereas the normal tissue of similar structure (Patient Co37) is totally unstained. Photographs were taken at 845× magnification on Kodak daylight film using a Wratten 80A filter and tungsten light source. Tissues were counterstained with hematoxylin/eosin.

As illustrated in Table 5, all (100%) of the breast cancer tissues stain positively for 16OHE-glucuronide fraction, and the near adjacent tissues (NAT) all stain strongly (++). The pattern of staining indicates that the greatest amount of 16OHE1-glucuronide fraction is found not in tumor, but in the NAT in which 40–100% of the sections stain, especially at the periphery of the malignant ductal and lobular structures. Of the 12 normal breast tissues, only 3 of 12 (25%) slow weak (±) staining for 16OHE1-glucuronide fraction, and in those cases staining is limited to hyperplastic, ectasic, or fibrocystic foci in breasts. The difference in staining between normal and cancerous tissues is highly significant ($p<0.009$). Staining in normal breast tissues is not associated with or proximal to ductal or lobular elements as is seen in breast cancer. As illustrated in Table 5, the presence of 16OHE1-glucuronide in breast carcinoma is not dependent upon the estrogen receptor status of tumor cells, as 4 of 8

(50%) tumors expressed estrogen receptors (ER), but all (100%) of the tumors stain strongly for 16OHE1-glucuronide fraction.

These findings further support consideration of said 16OHE1-glucuronide fraction as a tumor marker and tumor associated antigen. Immunohistochemical staining for 16OHE1-glucuronide fraction in breast cancer tumors, near adjacent tissues, and lymph nodes may be useful in determining the prognosis of a specific tumor, especially when used in conjunction with serum assays for serum 16OHE1-glucuronide fraction, high levels of 16OHE1-glucuronide fraction in tissues and serum could thus be considered as predictive for metastatic potential of a tumor.

TABLE 5

16OHE1-Glucuronide Fraction in Malignant and Normal Breast: Results in Formalin-Fixed Paraffin-embedded sections

|  | Breast Cancer | Controls* | P-value** |
|---|---|---|---|
| Fraction Positive (%)*** for 16aOHE1: |  |  |  |
|  | 100 % (8/8, ++) | 25% (3/12, +/−) | 0.009 |
| ER Status: | (4/8 ER +) | (12/12 ER +) |  |

*Normal breast tissues were obtained from breast reduction surgery.
**Kolmogorov-Smirnov Two-Sample Test
***Tissues were scored positive if more than 100% of cells stained.

EXAMPLE 4

Normal and Breast Cancer Sera in Direct ELISA for 2OHE1-Glucuronide Fraction

Ten sera from healthy women not taking estrogens or other drugs (from Jewish Hospital, St. Louis Mo. U.S.A.), and 16 sera from women with a history of breast cancer tumors undergoing mastectomy (from Case Western Reserve, Cleveland, Ohio, U.S.A., and Ohio State University, Columbus, Ohio, U.S.A.) were collected prospectively and assayed by the direct competitive assay for the 2OHE1-glucuronide fraction, herein after called "serum 2OHE1" as described above. The results are shown graphically in FIG. 8. Most of the surgeries were performed subsequent to earlier biopsies or lumpectomies that removed portions of the breast tumors.

The average of serum 2OHE1 for 8 postmenopausal women with localized, non-metastatic breast cancer tumors was about 140 pg/mL serum 2OHE1-glucuronide fraction. The presence or absence of tumor cell metastases to the lymphatic nodes system was known in these patients, that is, whether they were node positive or node negative, respectively. The 8 age-mathched women with positive nodes had about 53 pg/mL serum 2OHE1. The levels of serum 2OHE1 in 8 postmenopausal women with node negative disease were about 103 pg/mL, with none of the women having serum 2OHE1-glucuronide fraction above 170 pg/mL. The average serum 2OHE1 for the postmenopausal controls was highest of all groups, about 137 pg/mL serum. The serum 2OHE1 levels in node positive breast cancers were significantly lower than the controls (p<0.001) and node negative breast cancer group (p<0.05), respectively (FIG. 8). This data indicates that serum 2OHE1-glucuronide fraction is a marker for the potential metastatic spread of a breast cancer tumor. Odds Ratio analysis indicates that a breast cancer patient with serum 2OHE1<80 pg/mL would have at least a five-fold higher risk of developing metastatic breast cancer. The estrogen receptor status of the tumor must be considered, however. It also follows that the lower the level of serum 2OHE1 in a woman with breast cancer, the greater is the likelihood of metastatic spread of disease and/or occult tumor mass. Thee may be other situations, however, as in very early stage breast cancer, in which an elevated level of serum 2OHE1 may indicate the presence of an occult tumor.

These results further illustrate the utility of the level of serum 2OHE1 (the glucuronide fraction) as a marker for progression in estrogen sensitive malignancies.

EXAMPLE 5

Normal and Breast Cancer Tissue in APAAP Direct Immunocytochemical Assay for 2OHE1-Glucuronide Fraction Formalin-fixed paraffin-embedded breast tissue blocks from 12 healthy women undergoing breast reduction surgery, and blocks of breast tumor tissue and matched Near Adjacent Tissue (NAT) from 8 women with breast cancer were obtained from Ohio State University. Columbus, Ohio U.S.A. Tissue blocks were sectioned, dewaxed and stained for 2OHE1-glucuronide fraction as described above in APAAP Immunocytochemical Assay for said 2OHE1-glucuronide Fraction in Tissue Sections. Both tumor and matched NAT were stained for each tumor. Each tissue section was stained with four reagents: 1) monoclonal antibody to 2OHE1-glucuronide fraction; 2) monoclonal antibody to 2OHE1-glucuronide fraction with excess 2OHE1 added; 3) monoclonal antibody to 2OHE1-glucuronide fraction with excess estradiol added; and 4) nonimmune polyclonal mouse IgG at same concentration as specific monoclonal antibody. These last three stains acted as controls for specific and nonspecific staining. Thus, a pattern of specific staining would see: 1) positive; 2) negative; 3) positive; and 4) negative. The intensity of staining is ranked subjectively as negative (−), weakly positive (±), positive (+), and strongly positive (++).

Examples of breast tissues stained for 2OHE1 are illustrated in FIGS. 9A and 9B wherein a breast cancer tumor tissue and tissue from a normal breast are stained for 2OHE1-glucuronide fraction according to the APAAP direct immunocytochemical assay method of this invention. The breast tumor tissue (Patient 7450) demonstrates no staining of tumor cells, but nuclear staining of cells within an isolated duct of normal morphology (FIG. 9A). The normal tissue, unlike the tumor, shows numerous normal ducts in which the nuclei stain strongly for 2OHE1-glucuronide fraction (Patient Co78). Photographs were taken at 845x magnification on Kodak daylight film using a Wratten 80A filter and tungsten light source. Tissues were counterstained with hematoxylin/eosin.

All (100%) of the normal breast tissues stained positively for 2OHE1-glucuronide fraction, demonstrating localization of 2OHE1 to the nuclei of ductal epithelial cells. By contrast, 8/8 (0%) of the breast tumor tissues stained for 2OHE1. The NAT to all tumors stained positively (+) for 2OHE1. Of the 12 normal breast tissues, 12 of 12 (100%) showed (+) staining for 2OHE1-glucuronide fraction, and in those cases staining was limited to nuclei of ductal cells, and cytoplasm of normal stromal tissues (TABLE 6).

TABLE 6

2OHE1-Glucuronide Fraction in Malignant and Normal Breast:
Results in Formalin-Fixed Paraffin-embedded sections

|  | Breast Cancer | Controls* | P-value** |
|---|---|---|---|
| Fraction Positive (%)*** for 2OHE1: |  |  |  |
|  | 0%(8/8,−) | 100%(12/12,+ to ++) | 0.000 |
| ER Status: | (4/8 ER+) | (12/12 ER +) |  |

*Normal breast tissues were obtained from breast reduction surgery.
**Kolmogorov-Smirnov Two-Sample Test
***Tumor tissues scored positive if more than 10% of nuclei of cells stained.

These findings further support consideration of said 2OHE1-glucuronide fraction as a tumor marker and tumor associated antigen. Immunohistochemical staining for 2OHE1-glucuronide fraction in breast cancer tumors, near adjacent tissues, and lymph nodes may be useful in determining the prognosis of a specific tumor, especially when used in conjunction with serum assays for serum 2OHE1glucuronide fraction; high levels of 2OHE1-glucuronide fraction in tissues and serum could thus be considered as predictive for metastatic potential of a tumor.

EXAMPLE 6

Normal and Breast Cancer Sera in Direct ELISA for 2MeoE1-Glucuronide Fraction Twenty sera from healthy women not taking estrogens or other drugs (from Jewish hospital, St. Louis Mo. U.S.A.), and 12 sera from women with pathologically confirmed and staged breast cancer tumors at the time when serum was collected (from Case Western Reserve, Cleveland, Ohio, U.S.A., and Ohio State University, Columbus, Ohio, U.S.A.) were assayed by the direct competitive assay for 2MeoE1-glucuronide fraction, herein after called "serum 2MeoE1", and the data graphical shown in FIG. 10. Serum from these patients was collected on the day of surgery to remove the tumors by mastectomy. Most of the surgeries were performed subsequent to earlier biopsies or lumpectomies that removed portions of the breast tumors.

Only those women who were found to have residual malignant tissues are included in this study.

The average of serum 2MeoE1 for 20 healthy women was 24±13 pg/mL (±Standard Deviation). The presence or absence of tumor cell metastases to the lymphatic nodes system was known in these patients, that is, whether they were node positive or node negative, respectively. The 7 patients with positive nodes had an average of 75±15 pg/mL serum 2MeoE1, whereas 4 of 5 (80%), of the node negative patients had very significantly elevated serum 2MeoE1 (250±181 pg/mL). The difference between the node+and node−groups was highly significant (p<0.005, t-test). These data suggest that serum 2MeoE1-glucuronide fraction is a marker for metastatic potential of a breast cancer tumor, but in an opposite sense to that of serum 16OHE1-glucuronide fraction. Odds Ratio analysis indicates that breast cancer patients with serum 2MeoE1<(less than) 120 pg/mL would have at least a four-fold higher risk of having metastatic disease.

EXAMPLE 7

Longitudinal Monitoring of Chemotherapy of Breast Cancer with Direct ELISAS for 2OHE1-, 2MeoE1-, and 16OHE1-glucuronide fractions.

Serially collected serum samples (Bioclinical Partners, Waltham, Mass. U.S.A.) from two women undergoing chemotherapy for metastatic breast cancer were assayed for 2OHE1-, 2MeoE1-, and 16OHE1-glucuronide fractions by ELISAs of the present invention as described above.

Donor 13246 was a 76 year old woman with stage III breast cancer. She initially received a chemotherapy course with CMF (Cytoxan/Methotrexate/5-Flourouracil combination) treatment, followed by a series of treatments with adriamycin (FIG. 11). Clinically objective parameters indicated disease stability during CMF therapy, but relapse and progression soon after initiation of adriamycin treatments. Serum 16OHE1 glucuronide fractions were elevated above normal, and fell slightly during CMF therapy. By contrast, serum 2OHE1- and 2MeoE1-glucuronide fractions increased under CMF administration, but like 16OHE1, decreased abruptly after the initial treatment with adriamycin (FIG. 11. After this decline in all serum glucuronide fractions, however, the 16OHE1 serum levels rebounded sharply upward, whereas 2OHE1and 2MeoE1 concentrations remained depressed relative to levels before adriamycin treatments.

Donor 1709 was a 77 year old woman with advanced stage IV breast cancer. During the inital phases of serial monitoring, the disease, while advanced, was considered stable (FIG. 12). At a later time, however, a breif course of adriamycin was initiated. This treatment was poorly tolerated and/or ineffective, and a follow-up course of haotestin, an androgenic steroid, was given. Growth of the tumor in this woman was discovered to be progressing soon after initiation of adriamycin treatments (FIG. 12). Serum 16OHE1 glucuronide fraction was abnormally elevated initially in this woman, but declined somewhat prior to the beginning of first the chemotherapy treatment. After the initial adriamycin treatment, 16OHE1 increased sharply to a maximum, and then declined. By contrast, 2OHE1- and 2MeoE1-glucuronide fractions declined steadily after adriamycin treatments. It was at this time that clinical parametrs and tests indicated that the disease was in the early stages of progression (FIG. 12). The levels of 16OHE1 were unaffected by haotestin therapy, but serum 2OHE1- and 2MeoE1-glucuronide fractions increased sharply.

The above results suggest that a rising serum 16OHE1-glucuronide fraction where accompanied by relatively low levels of 2OHE1- and/or 2MeoE1-glucuronide fractions is predictive for progression of tumor growth in estrogen-sensitive cancers. There may be other circumstances, however, in which the glucuronide fractions may change in a different, yet predictive manner upon exposure to chemotherapy or other agents. Assays of the present invention as described herein will, therefore find broad utility in monitoring and predicting the clinical course of estrogen-sensitive cancers, including but not limited to cervical, ovarian, endometrial, uterine, and breast cancer.

EXAMPLE 8

ELISA Test Kit for 16OHE1-Glucuronide Fraction in Serum

All materials and reagents to perform the ELISA for serum 16OHE1-glucuronide are preferably packaged together in a single kit. The kit includes an antibody-coated microtiter plate (anti-mouse IgG Fc-specific antibody), a microtube rack (96×1.2 mL tubes), two adhesive microtiter plate covers, Sample Diluent containing monoclonal antibody to 16OHE1-glucuronide fraction (21 mL), Enzyme Conjugate Diluent (10 mL). 16OHE1-labeled-alkaline phosphatase (AP) (20 ul in 0.5 mL vial), AP Enzyme Substrate (paranitrophenylphosphate, pNPP) (21 ml), 16OHE1-3- glucuronide Standards (25–800 pg/mL) in charcoal-extracted serum (6×300 ul/vial), Positive Controls (2×300 ul/vial), a Negative Control (300 ul/vial), and Instructions for use of the Kit. The kit will determine serum 16OHE1-glucuronide in thirty-two serum samples. Compositions of kit components are as described in Direct ELISA for said 16OHE1-glucuronide Fraction in Serum, above.

EXAMPLE 9

APAAP Immunocytochemical Test Kit for 16OHE1-glucuronide Fraction in Tissues

All materials and reagents for immunostaining for 16OHE1-glucuronide fraction in fresh and/or paraffin-embedded fixed tissues may be brought together in a single kit. The kit includes 100 glass slide pretreated with swine serum, Anti-16OHE1 Antibody Solution (6 mL in dropper vial), Antibody Bridging Solution (6 mL in dropper vial), APAAP Complex (10 mL in dropper vial), Enzyme Substrate Solution (21 mL), 5 napthol AS-MX.Fast Red TR tablets, GVA Mount Solution (10 mL), TBS Wash and Dilution Buffer (5×30 mL, salts for reconstitution), and Instructions for use of the Kit. Negative and Positive Control Slides consisting of sectioned paraffin-embedded tissues mounted on swine serum-treated slides are included. Compositions of kit components are as described in APAAP Immunocytochemical Assay for 16OHE1-glucuronide Fraction in Tissue Sections, above. The kit will enable staining of at least 50 tissue sections.

Various modifications of this invention in addition to those shown and described herein will become apparent to those in the art from the foregoing description.

Such modifications are intended to be within the scope of the appended claims. The references herein cited are hereby incorporated by reference.

What is claimed is:

1. A method of screening for a pathology affecting estrogen-sensitive tissues of a human wherein an altered level of a metabolite of estrone and its respective 3-glucuronide is indicative of the pathology, or a susceptibility thereto, in said human which comprises:
    A. obtaining a urine, serum or tissue sample from said human in which said pathology is suspected;
    B. detecting the level of a particular metabolite of estrone and its respective 3-glucuronide from said sample;
    C. comparing this said level with the level derived from the testing of healthy humans to detect differences therefrom of said particular metabolite of estrone and its respective 3-glucuronide.

2. The method of claim 1 wherein said metabolites are selected from the group consisting of the products of enzymatic hydroxylation of estrone.

3. The method of claim 1 wherein said metabolites are selected from the group consisting of 2-hydroxyestrone, 16α-hydroxyestrone and 2-methoxyestrone.

4. The method of claim 1 wherein the 3-glucuronide is subjected to deconjugation to the free metabolite of estrone with the enzyme β-glucuronidase prior to analysis of tissue samples.

5. The method of claim 1 wherein said metabolite comprises 16α-hydroxyestrone and its 3-glucuronide.

6. The method of claim 1 wherein said metabolite comprises 2-hydroxyestrone and its 3-glucuronide.

7. The method of claim 1 wherein said metabolite comprises 2-methoxyestrone and its 3-glucuronide.

8. The method of claim 1 wherein said level is measured by immunochemical analysis.

9. The method of claim 8 wherein said immunochemical analysis is a competitive inhibition immunoassay.

10. The method of claim 9 wherein said immunochemical analysis is a competitive enzyme-linked immunoassay (ELISA) using monoclonal antibodies and 16α-hydroxyestrone (16OHE1)-enzyme conjugates which comprises:
    (a) adding to a microtiter plate coated with monoclonal antibody specific for 16α-hydroxyestrone (16OHE1)-3-glucuronide a sample of patient serum mixed with an enzyme covalently labeled with 16α-hydroxyestrone (16OHE1),
    (b) incubating the mixture from (a) for a period of incubation permitting competition between 16α-hydroxyestrone (16OHE1)-enzyme and serum 16α-hydroxyestrone (16OHE1)-glucuronide fraction for binding to monoclonal antibody bound to a solid phase;
    (c) washing the plate;
    (d) adding to the washed plate a color-generating enzyme substrate to determine the amount of 16α-hydroxyestrone (16OHE1)-enzyme bound; (e) determining the quantity of 16α-hydroxyestrone (16OHE1)-glucuronide fraction in each serum sample from the absorbance of the sample relative to a set of 16α-hydroxyestrone (16OHE1)-glucuronide standards and controls of known concentration; and
    (f) comparing the level of the 16OHE1-glucuronide fraction in the serum sample to an extrinsic numerical value derived either previously from the patient under testing, or from the testing of other subjects of the same species, to detect any differences in the level of said estrone metabolite and its glucuronide standards previously determined to ascertain the presence of abnormal levels of 16OHE1-glucuronide fraction indicative of a pathology.

11. The method of claim 10 wherein the assay is buffered so as to be kept acidic to protonate said glucuronide fraction, thereby minimizing charge interactions with proteins in tissues and body fluids.

12. The method of claim 10 wherein the assay is performed at 15 degrees Centigrade.

13. The method of claim 10 wherein said pathology is breast cancer.

14. The method of claim 9 wherein said innunochemical analysis is a competitive enzyme-linked immunoassay (ELISA) using monoclonal antibodies and 2-hydroxyestrone (2OE1)-enzyme conjugates which comprises:
    (a) adding to a microtiter plate coated with monoclonal antibody specific for 2-hydroxyestrone (2OE1)/2-hydroxyestrone (2OE1) 3-glucuronide a sample of patient serum mixed with an enzyme covalently labeled with 2-hydroxyestrone (2OE1),
    (b) incubating the mixture from (a) for a period of incubation permitting competition between 2-hydroxyestrone (2OE1)-enzyme and serum 2-hydroxyestrone (2OE1)-glucuronide fraction for binding to monoclonal antibody bound to a solid phase;
    (c) washing the plate;
    (d) adding to the washed plate a color-generating enzyme substrate to determine the amount of 2-hydroxyestrone (2OE1)-enzyme bound;
    (e) determining the quantity of 2-hydroxyestrone (2OE1)-glucuronide fraction in each serum sample from the absorbance of the sample relative to a set of 2-hydroxyestrone (2OE1)-glucuronide standards and controls of known concentration; and (f) comparing the level of the 2-hydroxyestrone (2OE1)-glucuronide fraction in the serum sample to an extrinsic numerical value derived either previously from the patient under testing, or from the testing of other subjects of the same species, to detect any differences in the level of said estrone metabolite and its glucuronide standards previously determined to ascertain the presence of abnormal levels of 2-hydroxyestrone (2OE1)-glucuronide fraction indicative of a pathology.

15. The method of claim 14 wherein the assay is buffered so as to be kept acidic to protonate said glucuronide fraction, thereby minimizing charge interactions with proteins in tissues and body fluids.

16. The method of claim 14 wherein the assay is performed at 15 degress Centigrade.

17. The method of claim 14 wherein said pathology is breast cancer.

18. The method of claim 9 wherein said immunochemical analysis is a competitive enzyme-linked immunoassay (ELISA) using monoclonal antibodies and 2-methoxyestrone (2MeoE1)-enzyme conjugates which comprises:

(a) adding to a microtiter plate coated with monoclonal antibody specific for 2-methoxyestrone (2MeoE1)/2-methoxyestrone (2MeoE1)-3-glucuronide a sample of patient serum mixed with an enzyme covalently labeled with 2-methoxyestrone (2MeoE1);

(b) incubating the mixture from (a) for a period of incubation permitting competition between 2-methoxyestrone (2MeoE1)-enzyme and serum 2-methoxyestrone (2MeoE1)-glucuronide fraction for binding to monoclonal antibody bound to a solid phase;

(c) washing the plate;

(d) adding to the washed plate a color-generating enzyme substrate to determine the amount of 2MeoE1-enzyme bound;

(e) determining the quantity of 2MeoE1-glucuronide fraction in each serum sample from the absorbance of the sample relative to a set of 2MeoE1-glucuronide standards and controls of known concentration; and (f) comparing the level of the 2MeoE1-glucuronide fraction in the serum sample to an extrinsic numerical value derived either previously from the patient under testing, or from the testing of other subjects of the same species, to detect any differences in the level of said estrone metabolite and its glucuronide standards previously determined to ascertain the presence of abnormal levels of 2MeoE1-glucuronide fraction indicative of a pathology.

19. The method of claim 14 wherein the assay is buffered so as to be kept acidic to protonate said glucuronide fraction, thereby minimizing charge interactions with proteins in tissues and body fluids.

20. The method of claim 14 wherein the assay is performed at 15 degrees Centigrade.

21. The method of claim 14 wherein said pathology is breast cancer.

22. The method of claim 1 wherein said level is measured in tissue.

23. The method of claim 22 wherein said level is measured by immunohistochemical detection.

24. The method of claim 23 wherein the method of immunohistochemical detection is by the alkaline phosphatase-anti-alkaline phosphatase (APAAP) method.

25. The method of claim 24 wherein the alkaline phosphatase-anti-alkaline phosphatase (APAAP) method comprises:

(a) incubating fixed tissue sections mounted on glass slides sequentially with:
1) mouse monoclonal antibody to said 16OHE1-glucuronide fraction; 2) rabbit polyclonal anti-mouse IgG antiserum, and 3) mouse anti-alkaline phosphatase:alkaline phosphatase immune complexes (APAAP) so that the rabbit anti-mouse IgG acts to bridge the primary monoclonal antibody to the APAAP complex, linking the two together;

(b) treating the tissue of step (a) with a color producing substrate for alkaline phosphatase to visualize the presence of tissue-bound APAAP, and hence tissue-bound antibody to said glucuronide fraction, by incubation of the treated tissue with a color producing substrate for alkaline phosphatase; and (c) observing the presence and location of color to indicate the presence and severity of the pathology.

26. The method of claim 25 wherein the tissue sections are formalin-fixed paraffin-embedded tissue sections.

27. The method of claim 25 wherein the coupling agent utilized is napthol phosphate and the capture agent utilized is Fast Red, to afford a bright red color for indicating the presence of the glucuronide fraction.

28. The method of claim 25 wherein the assay is buffered so as to be kept acidic to protonate said glucuronide fraction, thereby minimizing charge interactions with proteins in tissues and body fluids.

29. The method of claim 25 wherein said pathology is breast cancer.

30. The method of claim 24 wherein the alkaline phosphatase-anti-alkaline phosphatase (APAAP) method comprises:

(a) incubating fixed tissue sections mounted on glass slides sequentially with:
1) mouse monoclonal antibody to said 2-hydroxyestrone (2OHE1)-glucuronide fraction; 2) rabbit polyclonal anti-mouse IgG antiserum, and 3) mouse anti-alkaline phosphatase:alkaline phosphatase immune complexes (APAAP) so that the rabbit anti-mouse IgG acts to bridge the primary monoclonal antibody to the APAAP complex, linking the two together;

(b) treating the tissue of step (a) with a color producing substrate for alkaline phosphatase to visualize the presence of tissue-bound APAAP, and hence tissue-bound antibody to said glucuronide fraction, by incubation of the treated tissue with a color producing substrate for alkaline phosphatase; and (c) observing the presence and location of color to indicate the presence and severity of the pathology.

31. The method of claim 30 wherein the tissue sections are formalin-fixed paraffin-embedded tissue sections.

32. The method of claim 30 wherein the coupling agent utilized is napthol phosphate and the capture agent utilized is Fast Red, to afford a bright red color for indicating the presence of the glucuronide fraction.

33. The method of claim 30 wherein the assay is buffered so as to be kept acidic to protonate said glucuronide fraction, thereby minimizing charge interactions with proteins in tissues and body fluids.

34. The method of claim 30 wherein said pathology is breast cancer.

35. The method of claim 1 wherein said pathology is selected from neoplastic diseases such as endometrial cancer, breast cancer, cervical cancer, and combinations thereof.

36. The method of claim 35 wherein said pathology can be detected both pre- and post-operatively.

37. The method of claim 36 wherein said pathology is breast cancer.

38. The method of claim 37 wherein said detection can be used to determine the extent of lymph node involvement in breast cancer.

39. The method of claim 35 wherein said detection can be used to determine reccurrence of a neoplastic disease.

40. The method of claim 35 wherein said detection can be used to determine progression of the pathology and response to therapy.

41. A test kit for the screening of a pathology wherein an altered level of a metabolite of estrone and its respective 3-glucuronide is indicative of the pathology or a susceptibility thereto, using the serum, tissue or body fluid medium of a human under test, comprising:
(a) a predetermined amount of at least one detectably labeled immunochemically reactive estrone metabolite and its 3-glucoronide, or an antibody binding epitope thereof and;
(b) directions for use of said kit.

42. The test kit of claim 41 wherein the labeled immunochemically reactive component comprises antibodies to a 16α-hydroxyestrone (16OHE1)-glucuronide fraction consisting of 16α-hydroxyestrone (16OHE1) and 16α-hydroxyestrone (16OHE1)-3-glucuronide.

43. The test kit of claim 41 wherein the labeled immunochemically reactive component comprises antibodies to a 2-hydroxyestrone (2OE1)-glucuronide fraction consisting of 2-hydroxyestrone (2OE1) and 2-hydroxyestrone (2OE1)-3-glucuronide.

44. The test kit of claim 41 wherein the labeled immunochemically reactive component comprises antibodies to a 2-methoxyestrone (2MeoE1) glucuronide fraction consisting of 2-methoxyestrone (2MeoE1) and 2-methoxyestrone (2MeoE1)-3-glucuronide.

45. The test kit of claim 41 wherein the label is an enzyme or an enzyme pair.

46. The test kit of claim 45 wherein the label is selected from the group consisting of peroxidase, β-glucuronidase, β-D-glucosidase, β-D-galactosidase, urease, glucose oxidase plus peroxidase, galactose oxidase plus peroxidase, hexokinase plus GPDase, glucose oxidase plus alkaline phosphatase, NAD oxidoreductase plus luciferase, phosphofructokinase plus phosphoenol pyruvate carboxylase, aspartate aminotransferase plus phosphoenol pyruvate decarboxylase, and alkaline phosphatase.

47. The test kit of claim 41 wherein the label is a chemical which fluoresces.

48. The test kit of claim 47 wherein the chemical is selected from the group consisting of fluorescein, rhodamine, and auramine.

49. The test kit of claim 41 wherein the label is a radioactive element.

50. The test kit of claim 49 wherein the radioactive element is selected from the group consisting of $^{14}C$, $^{125}I$, $^{131}I$, $^{35}S$, $^{57}Co$, $^{59}Fe$ and $^{3}H$.

51. The test kit of claim 41 wherein the labeled immunochemically reactive component comprises the 16α-hydroxyestrone (16OHE1)-glucuronide fraction consisting of 16α-hydroxyestrone (16OHE1) and 16α-hydroxyestrone (16OHE1) glucuronide.

52. The test kit of claim 41 wherein the labeled immunochemically reactive component comprises the 2-hydroxyestrone (2OE1) glucuronide fraction consisting of 2-hydroxyestrone (2OE1) and 2-hydroxyestrone (2OE1)-3-glucuronide.

53. The test kit of claim 41 wherein the labeled immunochemically reactive component comprises the 2-methoxyestrone (2MeoE1)-glucuronide fraction consisting of 2-methoxyestrone (2MeoE1) and 2-methoxyestrone (2MeoE1)-3-glucuronide.

54. The method of claim 1 wherein the levels of the particular estrone metabolite and its 3-glucuronide are compared with levels obtained from previous testing of the same subject.

55. The method of claim 5 wherein levels of the sum of 16α-hydroxyestrone and its 3-glucuronide in blood serum and plasma are (mean±standard deviation): 40±17 pg/ml in healthy postmenopausal women.

56. The method of claim 7 wherein levels of the 2-methoxyestrone and its 3-glucuronide in blood serum and plasma are (mean±standard deviation): 24±13 pg/ml in healthy.

* * * * *